(12) United States Patent
Rihani et al.

(10) Patent No.: US 9,568,465 B2
(45) Date of Patent: Feb. 14, 2017

(54) BREATH ANALYSER AND DETECTION METHODS

(71) Applicant: Sharp Kabushiki Kaisha, Osaka (JP)

(72) Inventors: Samir Rihani, Oxford (GB); Tim Michael Smeeton, Oxford (GB)

(73) Assignee: Sharp Kabushiki Kaisha, Osaka (JP)

( * ) Notice: Subject to any disclaimer, the term of this patent is extended or adjusted under 35 U.S.C. 154(b) by 195 days.

(21) Appl. No.: 14/464,969

(22) Filed: Aug. 21, 2014

(65) Prior Publication Data
US 2016/0054294 A1   Feb. 25, 2016

(51) Int. Cl.
*G01N 33/497* (2006.01)
*G01N 21/27* (2006.01)
(Continued)

(52) U.S. Cl.
CPC ............ *G01N 33/497* (2013.01); *G01N 21/27* (2013.01); *G01N 21/33* (2013.01); *A61B 5/082* (2013.01);
(Continued)

(58) Field of Classification Search
CPC ...................... G01N 33/497; G01N 2033/4975; G01N 21/27; G01N 21/33; G01N 21/314; G01N 2021/2181; G01N 2201/062; G01N 2201/0627; G01N 2021/1704; A61B 5/082
(Continued)

(56) References Cited

U.S. PATENT DOCUMENTS 5,060,656 A   10/1991 Howard
6,479,019 B1   11/2002 Goldstein et al.
(Continued)

FOREIGN PATENT DOCUMENTS

JP   4-001557   1/1992
JP   10-078444   3/1998
(Continued)

OTHER PUBLICATIONS

Sahay P, et. al., Measurements of the Weak UV Absorptions of Isoprene and Acetone at 261-275 nm Using Cavity Ringdown Spectroscopy for Evaluation of a Potential Portable Ringdown Breath Analyzer, Sensors, Jun. 26, 2013, vol. 13, p. 8170-8187, ISSN 1424-8220.

(Continued)

*Primary Examiner* — Benjamin Schmitt
(74) *Attorney, Agent, or Firm* — Renner, Otto, Boisselle & Sklar, LLP

(57) ABSTRACT

A measurement device for measuring a concentration of a component of a gas mixture includes a chamber that contains the gas mixture, a light source that emits light into the chamber, the emitted light having a wavelength between 230 nm and 320 nm, and a light sensor that detects a portion of the light from the light source that has propagated through the gas mixture. A processor is configured to determine the concentration of the component of the gas mixture based on the portion of the light emitted from the light source that is detected by the light sensor. The light source may include one or more LEDs, each having a central wavelength of light emission between 270 nm and 320 nm and a linewidth of less than 50 nm. The device may be employed to determine acetone concentration in exhaled breath, which may be indicative of diabetes or other health conditions.

11 Claims, 10 Drawing Sheets

(51) Int. Cl.
*G01N 21/33* (2006.01)
*A61B 5/08* (2006.01)
*G01N 21/03* (2006.01)
*G01N 21/31* (2006.01)

(52) U.S. Cl.
CPC ........... *G01N 21/031* (2013.01); *G01N 21/314* (2013.01); *G01N 2021/3181* (2013.01); *G01N 2201/062* (2013.01); *G01N 2201/0627* (2013.01)

(58) Field of Classification Search
USPC ............ 73/23.3, 23.35, 23.4, 31.05; 600/532
See application file for complete search history.

(56) References Cited

U.S. PATENT DOCUMENTS

| | | | | |
|---|---|---|---|---|
| 6,599,253 | B1* | 7/2003 | Baum | A61B 5/0813 356/303 |
| 7,790,467 | B1 | 9/2010 | Massick | |
| 2002/0029003 | A1* | 3/2002 | Mace | A61B 5/083 600/532 |
| 2002/0143267 | A1 | 10/2002 | Montagnino | |
| 2003/0015019 | A1 | 1/2003 | O'Brien | |
| 2004/0017570 | A1* | 1/2004 | Parikh | A61B 5/097 356/437 |
| 2004/0137637 | A1 | 7/2004 | Wang et al. | |
| 2007/0249958 | A1* | 10/2007 | Martin | A61B 10/0012 600/551 |
| 2010/0002234 | A1 | 1/2010 | Cormier et al. | |
| 2010/0061885 | A1 | 3/2010 | Harley | |
| 2014/0209857 | A1 | 7/2014 | Takano et al. | |

FOREIGN PATENT DOCUMENTS

| | | |
|---|---|---|
| JP | 2012-013573 | 1/2012 |
| WO | WO 2011117572 A1 | 9/2009 |

OTHER PUBLICATIONS

Oscar B. Crofford et al., Acetone in breath and blood, Trans Am Clin Climatol Assoc. 1977; 88: 128-139.

Chuji Wang et al., An acetone breath analyzer using cavity ringdown spectroscopy: an initial test with human subjects under various situations, Aug. 27, 2008.

Sofian M. Kanan et al., Semiconducting Metal Oxide Based Sensors for Selective Gas Pollutant Detection, Oct. 16, 2009.

* cited by examiner

BREATH ANALYSER AND DETECTION METHODS

TECHNICAL FIELD

This invention relates to an apparatus for analysis of a gas mixture, and in particular for analysis of components in exhaled breath. More specifically the invention relates to systems and methods for measuring the concentration of acetone in breath for diabetes diagnosis/management or to monitor fat burning.

BACKGROUND ART

Using breath analysis for medical diagnosis is the subject of intense research effort. The non-invasive and real time nature of the measurement in addition to the ability to detect pathogenic changes at the molecular level are main advantages of this approach.

The concentration of specific biomarkers in human breath can be related to a symptom of a particular disease. For example, high concentrations of acetone in exhaled breath is known to be a biomarker of diabetes and of fat burning. The breath of non-diabetics typically contains ~0.5 parts per million (ppm) acetone. Elevated mean breath acetone concentration of ~0.8-4.0 ppm has been shown to exist in Type 1 and Type 2 diabetics. Some correlation between acetone concentration in breath and blood glucose levels has been suggested.

Diabetes is one of the most challenging problems for public health worldwide. It is a chronic disorder that affects the body's ability to use sugar as a source of energy, and consequently high blood sugar levels build up in the blood. People with diabetes either do not produce insulin (Insulin deficiency: type 1) or the production of insulin is not sufficient/effective (Insulin resistance: type 2). As a consequence of insulin resistance or deficiency, the human body is unable to use sugar as a source of energy, and therefore the body resorts to breaking down stores of fat and protein instead. This alternative source of fuel ultimately leads to elevated ketone concentration in the blood, including elevated acetone concentration. The acetone concentration in a person's exhaled breath is monotonically related to the concentration of acetone in their blood.

Since no cure is currently available, the condition requires lifelong management. In the case of type 1 diabetes, this includes keeping blood glucose levels within safe levels through frequent insulin injections or a continuous infusion of insulin through an insulin pump. For type 2 diabetes, blood glucose levels are managed through a combination of medication, diet, and exercise or insulin injections if necessary.

Furthermore, a life threatening condition known as diabetic ketoacidosis (DKA) can develop when very high levels of acetone in the blood are present. If this condition is not treated it can lead to diabetic coma or even death. Diabetic ketoacidosis accounts for around 50% of all diabetes-related hospital admissions in people with type 1 diabetes.

In order to manage blood glucose levels and prevent DKA, people with diabetes are required to frequently (typically 4 to 10 times a day) measure their blood glucose and in some cases their blood ketone levels. This is done using a small blood sample obtained through a painful and troublesome procedure requiring patients to prick their fingers each time a test is required.

Similar procedures may be used for diagnosis and screening. In the primary diagnosis a urine sample may be tested for the presence of ketones and/or glucose. Although this test is high in specificity, it has a very low sensitivity and is generally inconvenient.

In summary, current diabetes diagnosis and management methods/procedures generally have low sensitivity, are inconvenient, are painful to patients, and are time and money consuming. Therefore, extensive efforts worldwide are being devoted to find effective non-invasive methods for diabetes diagnosis and management.

Measurement of the concentration of acetone in a person's exhaled breath may be used as a means for diabetes diagnosis and diabetes management. However, due to the requirement to measure small acetone concentrations (typically in the range 0.1-10 ppm) and the presence of hundreds of different Volatile Organic Compounds (VOCs) in the human breath, no portable reliable acetone breath analyser for diabetes is currently available on the market.

For non-diabetic people, elevated breath acetone is mainly due to fat burning as a result of insufficient intake of carbohydrates to meet the metabolic needs of the body [O. B. Crofford et al., Acetone in breath and blood, Trans Am Clin Climatol Assoc. 1977; 88: 128-139]. Hence, if a patient is trying to lose weight this is a very useful index of success and can be used to encourage the patient.

Conventional breath analysis is conducted using gas chromatography coupled with a detection method, such as flame ionisation, ion mobility spectrometer, and mass spectrometer. These methods require bulky and expensive equipment as well as skilled operators, and therefore are not suitable for real time point-of-care testing.

Recently, cavity ringdown spectroscopy was used to measure the concentration of acetone in exhaled breath using light with ultraviolet (UV) or near-infrared (NIR) wavelengths [Wang et al, US20040137637 A1 (published Jul. 15, 2004); Wang et al., Measurement Science and Technology 19 105604 (published Aug. 27, 2008)]. This technique requires the use of lasers which are expensive components, especially at UV and NIR frequencies.

Graham et al., WO2011117572A1 (published Sep. 29, 2009) teaches use of a broadband NIR light source for breath acetone detection using a resonant optical cavity. This design determines acetone concentration in exhaled breath from a measurement of the absorption spectrum of the breath (i.e. the dependence of absorption in the breath on wavelength) at NIR wavelengths where acetone exhibits characteristic absorption. A broadband NIR light source is chosen which emits light over a range of wavelengths which is significantly broader than the range of wavelengths of a particular absorption band for acetone. The absorption spectrum is then measured using expensive components such as tunable filters, spectrometers, or gratings. Unfortunately, many other components in breath—such as VOCs or water vapour—exhibit strong absorption of infrared light which makes measurement at these wavelengths difficult and prone to absorption interferences.

Although metal oxide semiconductor sensors can be used for acetone detection, they suffer from poorly understood detection mechanism as well as low sensitivity. More importantly, they suffer from absorption interferences from other volatile organic compounds present in both air and breath, making them poor in terms of specificity [Kanan et al., Sensors 2009, 9, 8158-8196, published Oct. 16, 2009].

Other breath acetone detection methods include Massick, U.S. Pat. No. 7,790,467B1 (issued Sep. 7, 2010), which describes an indirect method based on the use of a diode laser emitting infrared light to detect a reaction by-product between acetone and hydrogen halide. Goldstein et al., U.S.

Pat. No. 6,479,019B1 (issued Nov. 12, 2002) describes a chemo-optical sensor where light absorption or transmission is a function of reaction with a target gas molecule such as acetone or other chemical. These methods are either complicated, have low detection limit, or suffer from low specificity.

An important issue with many of the above breath analysis methods is interference with other VOCs present either in ambient air or breath. Such interferences affect the sensitivity and specificity of the breath analyser.

Another related prior art is patent application Harely, US20100061885 A1 (published on Mar. 11, 2010), which discusses an instrument for determining Ozone concentration using a UV light source including LEDs.

SUMMARY OF INVENTION

Considering the drawbacks of conventional diabetes diagnosis and management methods, as well as limitations and issues of prior art breath acetone sensors, there is a need in the art for an inexpensive, portable, and user friendly apparatus that can provide an accurate diagnosis of diabetes through a non-invasive procedure such as acetone detection in the breath. Furthermore, there is a need in the art for such acetone breath analyser to overcome limitations of sensitivity and interferences with other VOCs.

The invention includes apparatuses and methods to measure the concentration of molecules including acetone in a gas mixture with high accuracy and low cost. The apparatus is suitable to determine the concentration of acetone in exhaled breath and may be applied for diabetes diagnosis, ketoacidosis diagnosis, fat burning monitoring and weight loss management.

In an aspect of the invention, the concentration of acetone in a gas mixture in a chamber is determined from the strength of absorption in the gas of light emitted by one or more solid-state deep UV light sources with wavelength between 230 nm and 320 nm (for example LEDs) using one or more simple photodetectors without the need for a spectrometer detector.

In an aspect of the invention, the apparatus includes one or more LEDs with a central emission wavelength in the range 270-320 nm and preferably in the range 285-320 nm; thereby providing very good accuracy even if other gases are present; particularly gases such as carbon dioxide and oxygen which are present in exhaled breath and/or ambient air and which would otherwise reduce the accuracy of acetone measurement based on absorption of deep UV light.

In another aspect of the invention, the apparatus includes one or more LEDs with a first central emission wavelength in the range 240-270 nm, and one or more LEDs with a second central emission wavelength in the range 270-300 nm. In another aspect of the invention, the apparatus includes one or more LEDs with a first central emission wavelength in the range 240-270 nm, and one or more LEDs with a second central emission wavelength in the range 270-290 nm, and one or more LEDs with a third central emission wavelength in the range 290-310 nm. In another aspect of the invention, the apparatus includes one or more LEDs with a first central emission wavelength in the range 200-240 nm, and one or more LEDs with a second central emission wavelength in the range 240-270 nm, and one or more LEDs with a third central emission wavelength in the range 270-300 nm. The use of two or three central emission wavelengths provides very good accuracy of acetone concentration measurement even if gases such as ozone or sulphur dioxide are present in exhaled breath and/or ambient air, and which would otherwise reduce the accuracy of acetone measurement based on absorption of deep UV light.

In another aspect of the invention, LEDs including $Al_yIn_xGa_{1-x-y}N$ materials are included in the light source or sources.

In another aspect of the invention, photodiodes—for example photodiodes including $Al_yIn_xGa_{1-x-y}N$ materials—are used as the photodetectors.

The invention further includes a method to determine the concentration of acetone in a gas mixture—for example exhaled breath—using the apparatus. This method may include a reference measurement made using ambient air. The method may further include measurements of temperature, pressure, oxygen concentration, and carbon dioxide concentration. The method may further include inputs of users' characteristics and environment characteristics.

In another aspect of the invention, a photodetector detects fluorescence (wavelength between 300 nm and 400 nm) from acetone to improve precision of the apparatus.

In another aspect of the invention, a multi-pass cell is used to increase the optical path length travelled by the UV light inside the chamber of the breath analyser.

In another aspect of the invention, an optical cavity is created using high reflectivity mirrors to significantly increase the optical path length travelled by the UV light inside the chamber of the breath analyser.

In another embodiment of the invention, a heating element, which could be optical or electrical, is included to heat up the gas sample (air or breath) or surfaces in contact with the gas sample.

In another embodiment, a light tight enclosure is used to prevent stray light from interacting with the gas inside the chamber or the photodetector. In particular, light tight valves are provided which enable gases to flow but do substantially block ambient light with wavelength between 300 nm and 700 nm from entering the chamber.

In another embodiment, a particle/dust filter is used to clean the gas before entering the chamber. The filter can also be used to remove moisture from the gas.

In another embodiment, the apparatus is used to detect and/or measure the concentration of ketones such as acetone in exhaled breath for the diagnosis of diabetes, diagnosis of ketoacidosis, or to monitor fat burning.

In another embodiment the apparatus is used to detect molecules emitted during the rancidification of foodstuffs.

The invention provides many advantages which are not suggested from the prior art. In particular, the invention provides for accurate measurement of acetone concentration using optical absorption from a simple apparatus including solid-state UV light sources (such as LEDs) without requiring a spectrometer. Several aspects of the invention provide, for the first time, an apparatus and a method of operation which provides reliable acetone concentration measurement even in the presence of interfering molecules such as oxygen, carbon dioxide, sulphur dioxide and ozone. Conventional configuration use a complex laser source with narrowband emission with 266 nm wavelength. This prior art does not identify or solve the problem associated with interference from all of these gas molecules listed above. In particular, conventional devices do not use one or more LEDs, with suitable first, second or third central emission wavelengths to obtain reliable results.

To the accomplishment of the foregoing and related ends, the invention, then, comprises the features hereinafter fully described and particularly pointed out in the claims. The following description and the annexed drawings set forth in detail certain illustrative embodiments of the invention.

These embodiments are indicative, however, of but a few of the various ways in which the principles of the invention may be employed. Other objects, advantages and novel features of the invention will become apparent from the following detailed description of the invention when considered in conjunction with the drawings. Furthermore, it will be understood, by those skilled in the art, that various modifications, additions and alterations may be made to the invention without departing from the spirit and scope of the invention as defined in the claims.

BRIEF DESCRIPTION OF DRAWINGS

In the annexed drawings, like references indicate like parts or features.

DESCRIPTION OF REFERENCE NUMERALS

Figure 1:
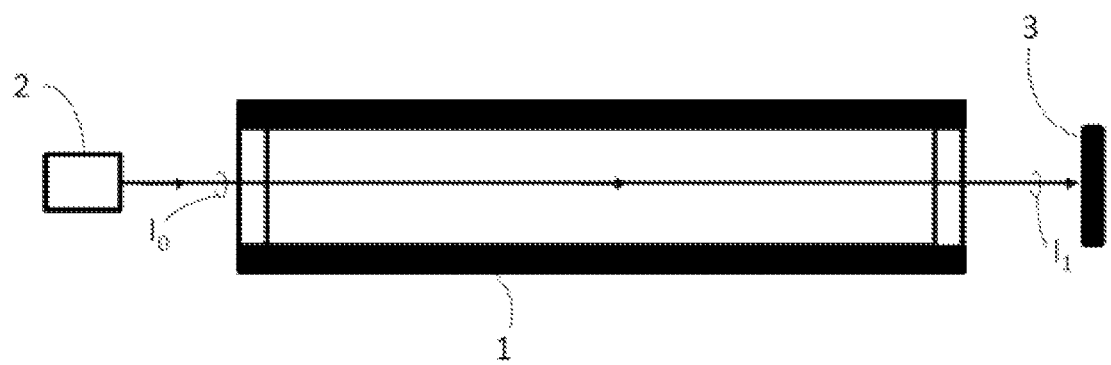
FIG. 1. An illustration of an apparatus to measure acetone concentration in a gas mixture FIG. 2. Plot of absorption cross section of acetone FIG. 3. Plot of absorption cross section of ozone FIG. 4. Plot of absorption cross section of sulfur dioxide FIG. 5. An illustration of an apparatus to measure acetone concentration in a gas mixture FIG. 6. A contour graph showing part per million (ppm) level error in Acetone measurement using absorption at two wavelengths FIG. 7. An illustration of an apparatus used to measure acetone concentration in a gas mixture using a light source in an example of the invention

1: a chamber
2: light source
3: photodetector
4: first light source
5: second light source
6: An example of a preferred measurement region
10: Apparatus to measure concentration of acetone (first example)
11: inlet valve
12: outlet valve
13: first window
14: second window
15: first photodetector
16: pressure release valve
17: light emitted by light source 2
18: first lens
19: beam splitter
20: second photodetector
21: gas occupying the chamber 1
22: second lens
23: photodetector
24: microprocessor
25: temperature sensor
26: pressure sensor
39: Apparatus to measure concentration of acetone (second example)
40: light emitted by light source 4
41: light emitted by light source 5
45: apparatus to measure concentration of acetone (third example)
46: apparatus to measure concentration of acetone (fifth example)
47: third photodetector
48: apparatus to measure concentration of acetone (sixth example)
49: mirror
55: first cavity mirror
56: second cavity mirror
57: lens
60: channel
61: interior walls of channel
62 entrance to channel
63: exit from channel
64: moving component in channel
65: heating element
66: heating element
67: filter

DETAILED DESCRIPTION OF INVENTION

The invention provides apparatuses and methods to detect and/or measure the concentration of molecules including acetone in a gas mixture with high accuracy and low cost. In one aspect of the invention, the concentration of acetone is determined from the strength of absorption of light emitted from one or more UV light sources, for example light emitting diodes (LEDs).

The absorption of light in a gas mixture generally depends on the absorption coefficient of the gas mixture to the light and the path length along which the light propagates through the gas. When light with wavelength $\lambda$ and initial intensity $I_0$ propagates through a gas mixture which has a wavelength-dependent absorption coefficient $\alpha(\lambda)$, the intensity of the light $I_1$ depends on the light path length L through the gas via the Beer-Lambert law:

$$\frac{I_1}{I_0} = \exp(-\alpha(\lambda)L) \quad (1)$$

The wavelength-dependent absorption coefficient α(λ), depends on the concentration of gas molecules in the gas mixture and the absorption cross-sections of the gas molecules. For gas containing one type of gas molecule with a concentration n and where the wavelength-dependent absorption cross-section of the gas molecule is σ(λ), the absorption coefficient is:

$$\alpha(\lambda)=\sigma(\lambda)n \quad (2)$$

Hence, by measuring light intensities $I_0$ and $I_1$ it is possible to determine the concentration of a gas n assuming that the absorption cross-section for the gas molecule and the path length of the light through the gas are known. The absorption cross section can be readily obtained from published databases, and the path length, or effective path length, is a property of the apparatus which can be measured.

For a gas mixture which contains more than one type of gas molecule, the absorption coefficient of the gas mixture may be determined from the sum of the absorption coefficients associated with each type of gas molecule. For example, if a gas mixture contains N different types of molecules each with absorption cross section $\sigma_i(\lambda)$ and concentration $n_i$ the absorption coefficient is $$\alpha(\lambda)=\Sigma_{i=1 \ to \ N} \sigma_i(\lambda)n_i \quad (3)$$

A significant challenge in producing an accurate sensor which uses the strength of absorption of light to determine the concentration of a first gas in a gas mixture is that gases other than the first gas may contribute to the absorption of the light. This problem is referred to as "cross-sensitivity" or "interference". A solution in the prior art to this problem is to measure and analyse the absorption spectrum of the gas mixture with high spectral resolution. An absorption spectrum is a measurement of the dependence of the absorption of light by the gas mixture on the wavelength of the light. One or more specific characteristic features of the absorption spectrum of the first gas can be identified in the absorption spectrum of the gas mixture, and thereby the concentration of the first gas may be determined without significant cross-sensitivity of other (unknown) gases in the gas mixture. A feature of this approach is that the range of wavelengths being measured and analysed in the absorption spectrum is wider than the wavelength range spanned by the one or more characteristic features in the absorption spectrum of the first gas. This requires complex optical design and components, such as a broadband light source and a spectrometer with high spectral resolution.

The present invention provides accurate measurement of acetone concentration in a gas mixture using absorption of deep UV light without requiring complex optical design and components. In an aspect of the present invention, the strength of absorption of the deep UV light emitted by light sources such as LEDs can be used to determine the concentration of acetone in the gas mixture, without requiring a spectrometer. An aspect of the invention, therefore, is measurement device for measuring a concentration of a component of a gas mixture. In exemplary embodiments, the measurement device includes a chamber for receiving a gas mixture, a light source that emits light into the chamber, the emitted light having a wavelength between 230 nm and 320 nm, and a light sensor that detects a portion of the light from the light source that has propagated through the gas mixture. A processor is configured to determine the concentration of the component of the gas mixture based on the portion of the light emitted from the light source that is detected by the light sensor. The light source may include one or more light emitting diodes (LEDs), each having a central wavelength of light emission between 270 nm and 320 nm and a linewidth of light emission of less than 50 nm. The device may be employed to determine acetone concentration in exhaled breath, which may be indicative of diabetes or other health conditions.

Referring to FIG. 1, the invention includes a chamber 1 which contains the gas mixture to be analysed, a light source 2 including one or more deep UV light emitting devices all emitting light with a central wavelength of approximately λ, and a photodetector 3 including one or more light sensitive devices which can be used to measure a power of deep UV light emitted from the light source 2 after the light has propagated through the gas mixture. The light source 2 preferably includes a solid-state deep UV light emitting device, for example an LED. The photodetector 3 preferably includes a solid-state light sensitive device, for example a photodiode.

Figure 2:
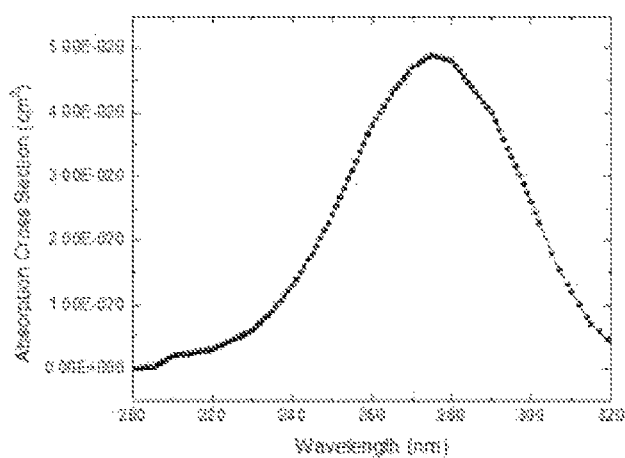

A plot of the absorption cross-section spectrum for acetone is shown in FIG. 2. Acetone absorbs deep UV light most strongly over a wide range of wavelengths between approximately 230 nm and 320 nm with a peak at approximately 275 nm. A feature of the present invention is that the spectral linewidth of the light emitted by the light source 2 may be narrower than the range of wavelengths where acetone absorbs deep UV light strongly, and the need for a spectrometer or other complex wavelength-measuring device is removed.

For example, the light source 2 may emit light with a linewidth less than or equal to 50 nm. The spectral linewidth of the light is a measure of the range of wavelengths which are present in the light. In this disclosure the spectral linewidth is defined as the full width at half maximum (FWHM) of the spectrum of the light. For example, the spectral linewidth is equal to the FWHM of a Gaussian function that has been fit to the spectrum using a conventional least-squares error method. In this case the central wavelength of the light (λ) may be defined as the central wavelength of said Gaussian function.

Figure 17:
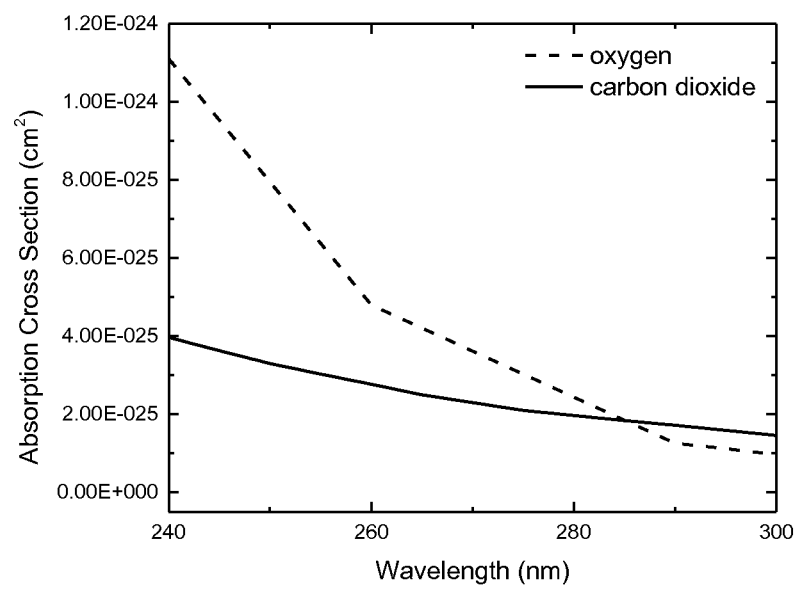
FIG. 17: Plot of absorption cross section of oxygen and carbon dioxide

An aspect of the current invention is that absorption of the deep UV light by gases in the gas mixture other than acetone are taken into account in the design and/or operation method of the apparatus so that the acetone concentration measurement is accurate and reliable. In a first example, the gas mixture is exhaled breath so that the acetone concentration in exhaled breath may be determined. To achieve an accurate and reliable sensor design in this case, the present inventors have found that it is very important to take into consideration the absorption of deep UV light by carbon dioxide ($CO_2$) and oxygen ($O_2$) in the design and/or operation method of the sensor. A plot of the approximate absorption cross-sections of carbon dioxide and oxygen is shown in FIG. 17. There are significant variations in the absorption cross-sections of oxygen that are reported in the scientific literature for the wavelength range between 240 nm and 300 nm. The present inventors have found that the absorption cross-section for oxygen that is plotted in FIG. 17 may be used to provide the advantage of the invention. However, other absorption cross-section values may also be used. Carbon dioxide and oxygen are both weakly absorbing at wavelengths between 240 nm and 300 nm. However, both gases may be present in a gas mixture with relatively high concentrations (for example as high as 30%) and therefore in some cases the total absorption of UV light by the gas should be taken into account to achieve an accurate and reliable sensor design.

To achieve an accurate sensor, it is also necessary to take into account other causes of reduction of the intensity of light incident on the photodetector 3. These other losses include scattering of light by gas molecules and reflection, absorption and scattering of light by optical components such as optical windows.

The invention overcomes these challenges and enables accurate measurement of acetone concentration in exhaled breath based on the core sensor structure shown in FIG. 1, through a specific process which is now described.

In this description, the following mathematical approximation is made to simplify the mathematical calculations:

$$\frac{I_1}{I_0} = \exp(-\alpha(\lambda)L) \cong 1 - \alpha(\lambda)L = 1 - \sigma(\lambda)nL \quad (4)$$

This approximation is appropriate if the absorption coefficients of the different gases are low but is not necessarily used in an implementation of the current invention.

Following from equations 1-4, the ratio of the optical power of light incident on the photodetector 3 ($I_1$) divided by the optical power of light incident on the first window ($I_0$) is given by:

$$\left(\frac{I_1}{I_0}\right)_{Breath} \cong 1 - \Sigma_j \sigma_j(\lambda) n_j L - \varepsilon = \quad (5)$$
$$1 - L(\sigma_{O_2}(\lambda) n_{O_2} + \sigma_{CO_2}(\lambda) n_{CO_2} + \sigma_{Ac}(\lambda) n_{Ac}) - \varepsilon$$

In this equation absorption of deep UV light in exhaled breath due to oxygen, carbon dioxide and acetone are explicitly taken into account and $\varepsilon$ represents all other losses. These additional losses include scattering of light by the gas molecules, reflection, absorption and scattering of light by optical components, and the collection solid angle of the photodetector. $n_{CO_2}$, $n_{O_2}$, and $n_{Ac}$ are the concentrations of carbon dioxide, oxygen and acetone in the exhaled breath respectively.

Many of the parameters included in Equation 5—in particular, $n_{CO_2}$, $n_{O_2}$, $n_{Ac}$ and $\varepsilon$—are not generally known. In order to determine the acetone concentration $n_{Ac}$ from measurement of $$\left(\frac{I_1}{I_0}\right)_{Breath},$$

an additional reference measurement may be made by introducing a reference gas into the chamber 1. The reference gas may be a pure gas such as nitrogen or a gas mixture such as ambient air.

For the reference gas:

$$\left(\frac{I_1}{I_0}\right)_{Ref} \cong 1 - \Sigma_j \sigma_j(\lambda) n_j L - \varepsilon' = \quad (6)$$
$$1 - L(\sigma_{O_2}(\lambda) n'_{O_2} + \sigma_{CO_2}(\lambda) n'_{CO_2} + \sigma_{Ac}(\lambda) n'_{Ac}) - \varepsilon'$$

Where $n'_{CO_2}$, $n'_{O_2}$, and $n'_{Ac}$ are the concentrations of carbon dioxide, oxygen and acetone in the reference gas respectively and $\varepsilon'$ represents all other losses, as in equation 5.

The reference gas in the chamber 1 may be at a pressure approximately equal to atmospheric pressure (1 atm), or the reference gas may be at a higher or lower pressure. For example, the reference gas in the chamber 1 may be at a pressure between $10^{-5}$ atm and 100 atm. The use of ambient air as the reference gas is a significant advantage for the sensor to be simple to use and to have low operating costs. The use of a reference gas at a pressure lower than atmospheric pressure may be advantageous to improve the accuracy of the sensor because absorption in the reference gas is reduced (compared with a reference gas at atmospheric pressure) and therefore $\varepsilon'$ maybe determined with high accuracy irrespective of the makeup of the reference gas.

In a preferred case, the concentration of acetone in the reference gas is zero (or negligibly small) and therefore equation 6 may be rewritten as:

$$\left(\frac{I_1}{I_0}\right)_{Ref} \cong 1 - \Sigma_j \sigma_j(\lambda) n_j L - \varepsilon = 1 - L(\sigma_{O_2}(\lambda) n'_{O_2} + \sigma_{CO_2}(\lambda) n'_{CO_2}) - \varepsilon' \quad (7)$$

If ambient air is used as the reference gas, it is generally a good approximation to assume $n'_{Ac}$ is zero or negligibly small.

From equations 5 and 7 we reach the following expression for the acetone concentration in the exhaled breath $$n_{AC} = \frac{L(\sigma_{O_2}(\lambda) \Delta_{O_2} + \sigma_{CO_2}(\lambda) \Delta_{CO_2}) + \left(\frac{I_1}{I_0}\right)_{Ref} - \left(\frac{I_1}{I_0}\right)_{Breath} + \varepsilon' - \varepsilon}{L \sigma_{Ac}(\lambda)} \quad (8)$$

Where, $\Delta_{O_2} = n'_{O_2} - n_{O_2}$ and $\Delta_{CO_2} = n'_{CO_2} - n_{CO_2}$ represent the concentration difference of oxygen and carbon dioxide between the exhaled breath and the reference gas, respectively.

The present inventors have determined that in many cases it is appropriate to assume that $\varepsilon = \varepsilon'$. This assumption is valid because scattering in exhaled breath and the reference gas—for example due to Raleigh scattering—are very similar. In other cases it is possible to determine a known relationship between $\varepsilon$ and $\varepsilon'$ for exhaled breath and a general type of reference gas.

Ambient air typically includes approximately 78% nitrogen, 21% oxygen and 0.04% carbon dioxide. However, the concentrations of these gases can vary between geographical location, local environment and altitude. For example, the concentration of carbon dioxide in the ambient air inside a building occupied by people may be higher than the concentration of carbon dioxide outside.

Human exhaled breath typically includes approximately 78% nitrogen, 16% oxygen and 5% carbon dioxide. However, the concentrations of these gases can vary depending on the concentration of the gases in the inhaled air (i.e. the environment) and between individual people and, for a single person, dependent on their health and exercise state.

Based on the typical concentrations described above for ambient air and exhaled breath, one can calculate typical values of $$\Delta_{O_2} = \frac{21\% - 16\%}{100\%} \frac{N_A}{V_m} \text{ and } \Delta_{CO_2} = \frac{0.04\% - 5\%}{100\%} \frac{N_A}{V_m},$$

where $N_A$ is Avogadro's number and $V_m$ is the molar volume of a gas (for example an ideal gas) for relevant temperature and pressure. Using these values and equation 8, it is possible to determine the concentration of acetone in exhaled breath from a measurement of $$\left\{\left(\frac{I_1}{I_0}\right)_{Ref} - \left(\frac{I_1}{I_0}\right)_{Breath}\right\},$$

and either assuming $\epsilon=\epsilon'$ or taking into account and known relationship between $\epsilon$ and $\epsilon'$.

In an aspect of the invention, suitable values of $\Delta_{O_2}$ or $\Delta_{CO_2}$ are identified depending on inputs such as data about the local environment (for example, geographical location, altitude, rural or urban, indoors or outdoors) and the individual whose exhaled breath is under analysis (for example sex, age, health, exercise state, respiratory performance). In another aspect of the invention, typical values of $\Delta_{O_2}$ or $\Delta_{CO_2}$ are used (such as described above) without requiring information about the local environment or the individual whose breath is under analysis.

In a further aspect of the invention, one or more sensors may be used to measure the concentration of at least one of oxygen and carbon dioxide in the exhaled breath and the reference gas to provide suitable values of $\Delta_{O_2}$ and/or $\Delta_{CO_2}$.

The use of equation 8 requires knowledge of the absorption cross-sections of acetone ($\sigma_{Ac}(\lambda)$), carbon dioxide ($\sigma_{CO_2}(\lambda)$) and oxygen ($\sigma_{O_2}(\lambda)$) to the light emitted by the light source 2. Suitable values are plotted in FIG. 2 for acetone and FIG. 17 for oxygen and carbon dioxde, but other values may be used. Therefore, suitable values of $\sigma_{Ac}(\lambda)$, $\sigma_{CO_2}(\lambda)$ and $\sigma O_2(\lambda)$ may be identified according to knowledge of the wavelength or wavelengths of light emitted by the light source 2.

The light source 2 may include a laser, for example a laser diode or a laser which includes an optically pumped laser crystal and may be optically pumped by a laser diode. The laser may directly emit light with a central wavelength of approximately $\lambda$. Alternatively, the light emitted by the laser may undergo a frequency-conversion process to generate light with a central wavelength of approximately $\lambda$. For example, the light emitted by the laser may propagate through a component which doubles the frequency of the light through a process such as second harmonic generation. In the case that the light source 2 includes a laser, the spectral linewidth of the light emitted by the light source may be less than 2 nm and may be less than 1 nm.

The light source 2 may include a broad band light emitting diode (LED) which emits light with a central wavelength of approximately $\lambda$. In this case the spectral linewidth of the light may be between 5 nm and 40 nm.

The light source 2 may include a phosphor material which converts light with a first wavelength into the light with a central wavelength of approximately $\lambda$. For example, the light source 2 may include a laser or a LED to generate light with a first wavelength. Light with the first wavelength may then irradiate a phosphor material such that light with the first wavelength is absorbed by the phosphor material and light with a central wavelength of approximately $\lambda$ is emitted by the phosphor material.

In a preferred case the light with a central wavelength of approximately $\lambda$ which is emitted by the light source 2 has a spectral linewidth which is less than or equal to 50 nm. In a more preferable case the spectral linewidth is less than or equal to 50 nm and greater than or equal to 5 nm. In a still more preferable case the spectral linewidth is less than or equal to 30 nm and greater than or equal to 5 nm. And in a still more preferable case the spectral linewidth is approximately 10 nm.

It is advantageous to use light with a spectral linewidth described in the above examples because this provides a device which is low cost and has high performance for reasons which will now be explained. The spectral linewidth should preferably be less than or equal to 50 nm to provide highly specific measurement of concentration of a target molecule (e.g. acetone in this example) with a simplified detection system. When the spectral linewidth of the light emitted by the light source 2 is less than or equal to 50 nm, the linewidth of said light is similar to or lower than the range of wavelengths over which a target molecule such as acetone is strongly absorbing (for example the range of wavelengths over which the molecule absorbs light by at least 10% of the maximum absorption by the molecule in the 230-320 nm wavelength range). Therefore, a substantial fraction of the wavelengths of light emitted by the light source 2 may be absorbed by a target molecule such as acetone. This means that the detection system (for example the photodetector 3) requires lower sensitivity than if the linewidth of the light emitted by the light source 2 was significantly larger than the range of wavelengths over which a target molecule such as acetone is strongly absorbing. Furthermore, when the spectral linewidth of the light emitted by the light source 2 is less than or equal to 50 nm, the absorption from a target molecule such as acetone may be distinguished from absorption by other molecules in the gas mixture through the careful selection of the central wavelength of the light source. This enables a sensor without need for a spectrometer.

It is advantageous to use light with a spectral linewidth greater than or equal to 5 nm because then the sensor accuracy may not be strongly reduced by variation in the central wavelength of the light. The central wavelength of the light emitted by the light source 2 may change due to a change in ambient temperature, due to ageing of the light source 2, due to a change in operating conditions such as the voltage or electrical injection current applied to the light source 2, or due to another reason. If the spectral linewidth of the light emitted by the light source 2 is very small (e.g. less than 1 nm), a small change in the central wavelength can lead to a significant change in absorption by molecules in the gas mixture. This is especially the case if the absorption spectrum of the molecule includes "narrow" features where the absorption changes significantly for a small change in wavelength. For example, the absorption spectrum of oxygen includes "narrow" features, the so-called "Herzburg lines" (these are not visible in FIG. 17 because that spectrum is sampled relatively coarsely along the wavelength axis). If the light emitted by the light source 2 has a spectral linewidth greater than or equal to 5 nm, the absorption is much less affected by a change in the central wavelength than if the spectral linewidth is very small (e.g. less than 1 nm). Therefore inaccuracy in the acetone concentration measurement due to a change in the central wavelength of the light emitted by the light source 2 is made small.

A further advantage of use of light with a spectral linewidth greater than or equal to 5 nm is that the sensor may not be strongly reduced by variation in ambient temperature of the gas mixture. Changes in ambient temperature may change the absorption spectra of molecules which are present in the gas mixture. In particular, the wavelength of "narrow" features in the absorption spectrum as described above may change. If the light emitted by the light source 2 has a linewidth greater than or equal to 5 nm then absorption is much less affected by a change in the absorption spectra of molecules which are present in the gas mixture. Therefore, inaccuracy in the acetone concentration measurement due to a change in the ambient temperature of the gas mixture is made small.

A preferred choice of a deep UV light emitting device in the light source 2 is a LED. In general deep UV LEDs do not emit a single wavelength, but actually emit light with a linewidth in the range between 5 nm and 30 nm. The emission spectrum of an LED may be defined by the function $\chi(\lambda)$. Sometimes $\chi(\lambda)$ can be quite well approximated by a Gaussian variation. A feature of the present invention is that the photodetector 3 measures the total power of one or more wavelengths emitted by the light source 2 in the range 230-320 nm, after propagation through the chamber 1. Therefore, it is preferable that each of the absorption cross-section values used in equation 8 are calculated taking account of the wavelength spread of the light source 2. For example, if the photodetector 3 measures the power between wavelength $\lambda_{min}$ and $\lambda_{max}$:

$$\sigma_{LED} = \frac{\int_{\lambda_{min}}^{\lambda_{max}} \chi(\lambda)\sigma(\lambda)d\lambda}{\int_{\lambda_{min}}^{\lambda_{max}} \chi(\lambda)d\lambda}. \quad (9)$$

The process described above provides a good general method to determine the concentration of acetone in exhaled breath using a simple apparatus. However, there are uncertainties in some of the assumed parameters. In particular, equation 8 requires estimates of $\Delta_{O_2}$ and $\Delta_{CO_2}$. As described above, good typical estimates may be measured or assumed—for example for exhaled breath and ambient air—but these estimates will sometimes be erroneous to some extent. Deviation between the actual and assumed values of $\Delta_{O_2}$ and $\Delta_{CO_2}$ may result in a less accurate determination of $n_{Ac}$.

An aspect of the present invention is to provide a robust method to determine the concentration of acetone in spite of these uncertainties. From study of FIG. 2 there is clear benefit to using deep UV light with wavelength close to 275 nm at which the absorption due to acetone is strongest. In principle the strongest absorption enables detection of smaller acetone concentrations and one skilled in the art would naturally prefer a deep UV LED with central wavelength of approximately 275 nm. However, through detailed analysis of the consequence of uncertainties in $\Delta_{O_2}$ and $\Delta_{CO_2}$ on the accuracy of the acetone concentration measurement, the present inventors have determined that it is a significant advantage to use central wavelengths significantly longer than 275 nm to provide a sensor with high accuracy in real applications. In particular, central wavelengths of the light source 2 of at least 285 nm, and preferably central wavelengths in the range between 290 nm and 300 nm are strongly preferred. Use of these longer wavelengths provides a much more accurate measurement of the acetone concentration in operational environments, even though the absorption cross-section is approximately one half of the value that would apply for use of a 275 nm central wavelength.

Figure 3:
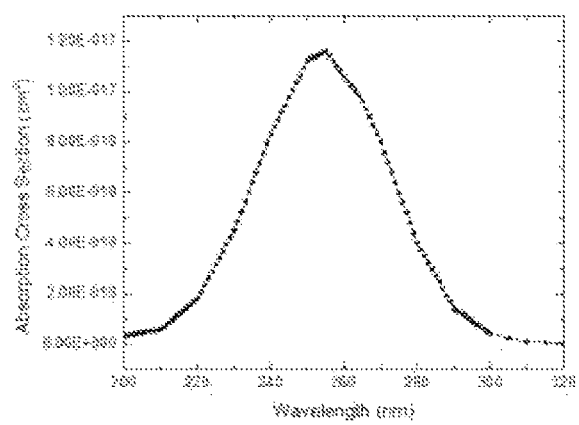

The invention as described above provides an excellent solution to the need to measure acetone in a gas mixture—such as exhaled breath—with low cost and high accuracy. It is particularly suitable for measurement in situations where the concentration of ozone ($O_3$) in both the reference gas and the exhaled breath are negligibly low (<0.001 ppm). However, the present inventors have determined that the accuracy of the acetone concentration measurement according to the invention described above (e.g. FIG. 1) can be reduced if ozone is present in either the reference gas or the exhaled breath. The absorption cross-section spectrum for ozone is plotted in FIG. 3. Ozone absorbs deep UV light with wavelength between 210 nm and 320 nm with a peak absorption for a wavelength of approximately 255 nm. The concentration of ozone in ambient air depends strongly on the local environment but is typically ~0.08 ppm. 0.08 ppm of ozone absorbs 275 nm wavelength light 10 times more strongly than 1 ppm acetone.

One way to overcome this problem is to use an ozone filter in order to remove ozone from reference gas and/or the exhaled breath. An example of an ozone filter is potassium iodide. A disadvantage of using an ozone filter such as potassium iodide is that they can be non-efficient and will need replacing after saturation. Furthermore, such filters may also affect acetone in the breath and may therefore lead to an inaccurate measurement.

An aspect of the invention is to improve the accuracy of acetone measurements when ozone may be present, without requiring an ozone filter. In a first aspect of this improvement, the central wavelength of the light source 2 should lie in the range from 300 nm to 320 nm. For example, the light source 2 should include one or more deep UV LEDs with central wavelength in range from 300-320 nm. This wavelength range is preferred because the absorption by ozone of 300-320 nm wavelength light is very significantly lower than for 275 nm wavelength light, and the ratio of the absorption cross-section of acetone divided by the absorption cross section of ozone for 300-320 nm wavelength light is significantly higher than for 275 nm wavelength light (as explained above, 275 nm wavelength which would be a natural choice of wavelength based on analysis of the acetone absorption spectrum).

Another aspect of the invention is to further improve the accuracy of acetone measurement through use of two different light sources emitting deep UV light with different central wavelengths. This provides further robustness against uncertainties in the concentration of the reference gas, especially in the case that ozone may be present with unknown concentration.

In what follows we describe an alternative method to address absorption interference from ozone, by way of example. The method however, can be generalised to address any interference from any potential gas mixture or reference gas component.

Figure 5:
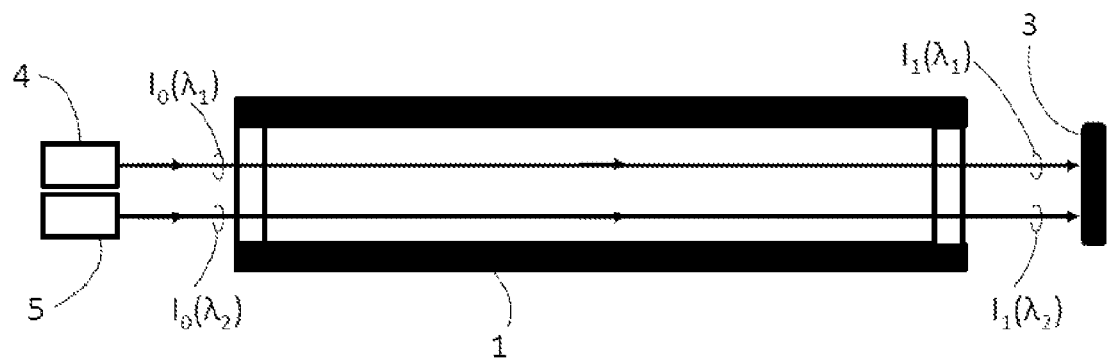

FIG. 5 shows the core elements of this aspect of the invention. A first light source 4 includes one or more deep UV light emitting devices all emitting light with approximately a first central wavelength $\lambda_1$. A second light source 5 includes one more deep UV light emitting devices all emitting light with approximately a second central wavelength $\lambda_2$. A chamber 1 contains a gas or gas mixture and one or more photodetectors 3 measure a power of deep UV light emitted from the first light source 4 and/or second light source 5 after the light has propagated through the gas or gas mixture in chamber 1. A single photodetector may be used to measure the power of the deep UV light either emitted from the first light source 4 or the second light source 5. Alternatively different photodetectors may be used to measure the power of the deep UV light emitted from the first light source 4 and the second light source 5.

Following similar mathematical derivation as described above, the acetone concentration in exhaled breath $n_{Ac}$ may be determined from measurements of $$\left\{ \left(\frac{I_1}{I_0}\right)_{Ref} - \left(\frac{I_1}{I_0}\right)_{Breath} \right\}$$

at the first and second wavelengths using equation 10:

$$\begin{bmatrix} \Delta O_3 \\ n_{Ac} \end{bmatrix} = \frac{1}{\sigma_{O_3}^{\lambda_1}\sigma_{Ac}^{\lambda_2} - \sigma_{Ac}^{\lambda_1}\sigma_{O_3}^{\lambda_2}} \begin{bmatrix} \sigma_{Ac}^{\lambda_2} & -\sigma_{Ac}^{\lambda_1} \\ -\sigma_{O_3}^{\lambda_2} & \sigma_{O_3}^{\lambda_1} \end{bmatrix} \begin{bmatrix} x' \\ y' \end{bmatrix} \quad (10)$$

where x' and y' are:

$$x' = \frac{x}{L} - \sigma_{O_2}^{\lambda_1}\Delta_{O_2} - \sigma_{CO_2}^{\lambda_1}\Delta_{CO_2} \quad (11)$$

$$y' = \frac{y}{L} - \sigma_{O_2}^{\lambda_2}\Delta_{O_2} - \sigma_{CO_2}^{\lambda_2}\Delta_{CO_2} \quad (12)$$

and where x and y are:

$$x = \left(\frac{I_1}{I_0}\right)_{Ref}^{\lambda_1} - \left(\frac{I_1}{I_0}\right)_{Breath}^{\lambda_1} \quad (13)$$

$$y = \left(\frac{I_1}{I_0}\right)_{Ref}^{\lambda_2} - \left(\frac{I_1}{I_0}\right)_{Breath}^{\lambda_2} \quad (14)$$

$\Delta O_3$ is defined similarly to $\Delta O_2$ above as the difference between the concentration of ozone in the reference and in the exhaled breath. $\Delta O_3$ is an unknown parameter which may also be calculated using equation 10.

Equation 10 provides a general solution to determine the acetone concentration in exhaled breath with high accuracy even if ozone may be present with unknown concentration in either the reference gas or the exhaled breath. The first and second central wavelengths are in the range between 230 nm and 320 nm.

Figure 6:
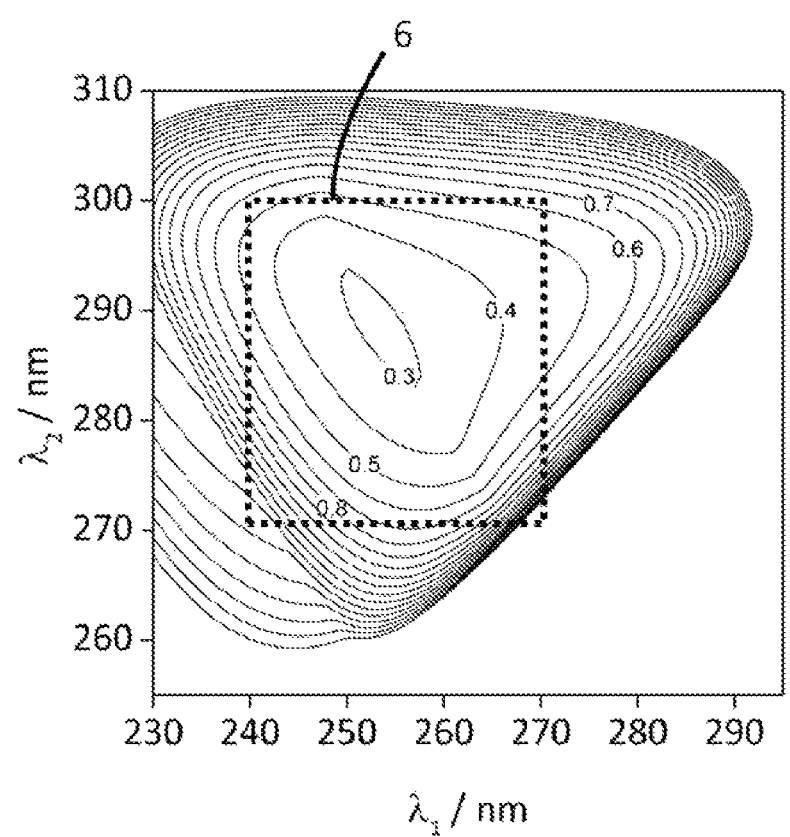

A further aspect of the present invention is the selection of the first and second central wavelengths to obtain the highest possible accuracy acetone measurement. The contour plot in FIG. 6 shows the error (in ppm) in acetone concentration for multiple combinations of $\lambda_1$ and $\lambda_2$. This contour plot was determined for a nominal (real) acetone concentration of 0.5 ppm and taking account of instrumental noise associated with measurements of x and y, for an ambient air reference gas and assuming that $\Delta_{O_2}$ and $\Delta_{CO_2}$ vary over ranges consistent with a wide range of ambient environments and exhaled breath conditions.

The contour plot in FIG. 6 shows that the lowest uncertainty in acetone concentration measurement is obtained for a first central wavelength of approximately 255 nm and a second central wavelength of approximately 290 nm. The region of highest accuracy is labelled as 6 and corresponds to a first central wavelength in the range between 240 nm and 270 nm and a second central wavelength in the range between 270 nm and 300 nm.

Figure 4:
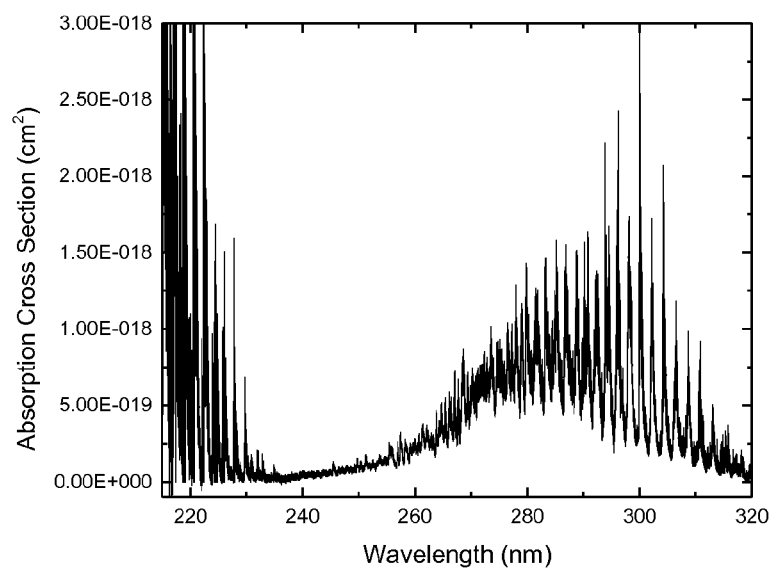

In another aspect of the invention, the accuracy of the acetone concentration measurement may be further improved in the case that the concentration of sulphur dioxide ($SO_2$) in either the gas mixture or the reference gas are not negligibly small. The present inventors have found that presence of $SO_2$—such as are caused by urban pollution—can result in reduced accuracy of the acetone concentration measurement according to the invention described thus far. The absorption spectrum of $SO_2$ is plotted in FIG. 4. In this case it may be preferred to include a light source with a third central wavelength in addition to the first and second wavelengths described so far. In particular, reliable acetone concentration measurement may be obtained using a first central wavelength in the range between 240 nm and 270 nm, a second central wavelength in the range between 270 nm and 290 nm and a third central wavelength in the range between 290 nm and 310 nm.

Alternatively, even greater accuracy may be obtained using a first central wavelength in the range between 200 nm and 240 nm (for example approximately 219 nm), a second central wavelength in the range between 240 nm and 270 nm and a third central wavelength in the range between 270 nm and 300 nm. In this case it may be advantageous for the light with the first central wavelength to have a linewidth of less than 1 nm, owing to the "narrow" absorption features in sulphur dioxide at wavelength between 200 nm and 240 nm. For example the light with the first central wavelength may be emitted by a laser source, preferably including a frequency-conversion process such as second harmonic generation.

The techniques described above can be extended to other molecules which may be present in the gas mixture or the reference gas. Furthermore, it may be possible to use more than three deep UV wavelengths in order to address the issue of interference and, by way of error analysis as described above, it is also possible to determine the most suitable wavelengths to use in order to minimise errors in acetone measurement.

The invention may also be used to measure the concentration of molecules other than acetone in a gas mixture. For example, the invention may be applied to measure the total concentration of one or more types ketone molecule in a gas mixture (acetone is an example of a ketone), or indeed the concentration of any volatile organic compound (VOC) molecule. The invention may be applied to any gas mixture other than exhaled breath.

Furthermore, although the invention has been introduced mostly in the context of a sensor where the gas mixture is exhaled breath, the sensor may be applied on other applications. For example, the sensor may be used to detect rancidification (e.g. oxidative rancidification) such as occurs to foodstuffs. Oxidative rancidification occurs due to reaction of oxygen with constituents of foodstuff (e.g. fats and oils) and results in formation of molecules including ketones and aldehydes. The sensor according to the present invention may be applied in devices to detect these molecules in the gas mixture around a foodstuff and thereby to detect rancidification.

The invention provides many advantages which are not achieved in conventional configurations from the prior art. In particular, the invention provides for accurate measurement of acetone concentration using optical absorption from a simple apparatus including solid-state UV light sources (such as LEDs) without requiring a spectrometer. Several aspects of the invention provide, for the first time, an apparatus and a method of operation which provides reliable acetone concentration measurement even in the presence of interfering molecules such as oxygen, carbon dioxide, sulphur dioxide and ozone. A conventional acetone sensor using a UV source in the prior art uses a complex laser source with narrow linewidth emission with 266 nm wavelength (linewidth less than 1 nm). This configuration does not address problems associated with interference from all of these gas molecules listed above. In particular, conventional configuration do not use one or more LEDs, suitable first, second or third central wavelengths to obtain reliable results.

EXAMPLE 1

Single-Wavelength Sensor

Figure 7:
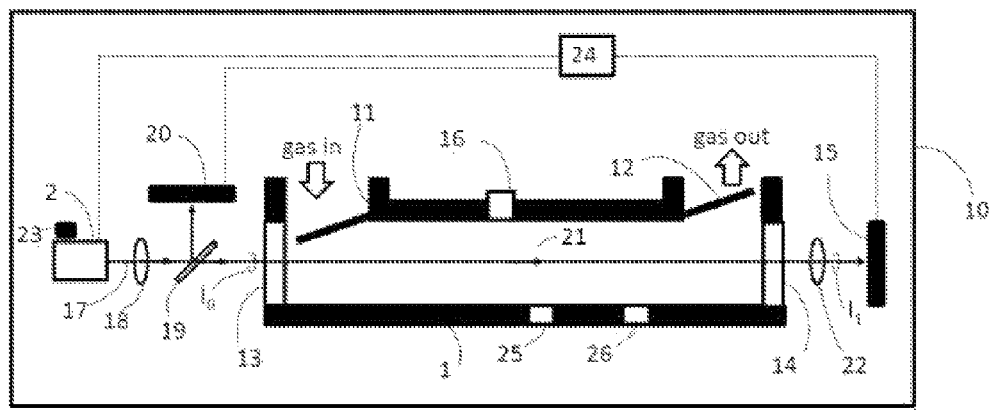

A first example of an apparatus to measure the concentration of acetone in exhaled breath is illustrated in FIG. 7. The apparatus 10 includes a chamber 1, an inlet valve 11, an outlet valve 12, a first window 13, a second window 14, a light source 2 and a first photodetector 15. The inlet valve 11 may be opened to allow a gas to flow into the chamber 1 and may be closed to seal the chamber. The outlet valve 12 may be opened to vent the gas from the chamber to allow gas to flow out of the chamber, and the valve 12 may be closed to seal the chamber. The inlet valve 11 and outlet valve 12 are preferably "light tight" so that ambient light does not enter the chamber 1 when the valves are closed. Ambient light is any light which is not emitted by the light source 2. For example, ambient light may be due to sunlight or artificial lighting in the location where the apparatus is used. Gas may be drawn into or out of the chamber using a micropump, a syringe or another method. The pressure of the gas in the chamber may be controlled by an optional pressure release valve 16. The pressure of the gas in the chamber may be the same as or similar to atmospheric pressure.

The first window 13 transmits light from the light source into the chamber, and the second window 14 transmits light from the chamber to the light sensor. The first window 13 and second window 14 preferably both have high transparency (for example, more than 50%) to light emitted by the light source 2. Suitable materials for the windows include UV fused silica, quartz, PMMA, PTFE, fluourinated ethylene propylene and other fluoropolymers, but many other materials are also suitable. Either or both of the surfaces of the first and second windows may include coating which reduces the reflection of the light emitted by the light source 2 from said surface or surfaces.

The light source 2 emits light with wavelength or wavelengths between 230 nm and 320 nm. The light source 2 may emit light with a single wavelength or light with a range of wavelengths about a central wavelength. The light source 2 may include one or more solid-state light sources such as LEDs. The light source 2 may emit light with a linewidth of between 5 nm and 30 nm or approximately 10 nm. For this example, the light source 2 is a LED containing $Al_yGa_{1-y}N$ materials (where $0 \leq y \leq 1$) and emits light with a central wavelength of approximately 285 nm. Alternatively, the LED may be an $Al_yIn_xGa_{1-x-y}N$ material where $0 \leq x \leq 1$ and $0 \leq y \leq 1$ and x+y is less than approximately 1. Light 17 emitted by the light source 2 may be focused or collimated using an optional first lens 18. The optional first lens 18 may be attached to the package of the light source 2. An optional beam splitter 19 may reflect some (for example, between 5% and 50%) of the light 2 towards an optional second photodetector 20. The second photodetector 20 may be used to determine the power emitted by the light source 2. In particular, the second photodetector 20 may be used to identify any relative value of $I_0$ (the power of the light 17 which is incident on the first window 13).

The first photodetector and second photodetector may include photodiodes. For example, the photodetectors may include silicon-based photodiodes, or $Al_yGa_{1-y}N$-based photodiodes (where $0 \leq y \leq 1$), or an $Al_yIn_xGa_{1-x-y}N$ material where $0 \leq x \leq 1$ and $0 \leq y \leq 1$ and x+y is less than approximately 1. The first and second photodetectors detect light with wavelength or wavelengths of the light 17. A filter may be included on the photodiodes such that some or all of the light incident on the filter which has a wavelength longer than the $\lambda_c$ does not reach the photodiode. $\lambda_c$ may be in the range from 300 nm to 450 nm. Alternatively, the photodiode may be chosen such that it has very low sensitivity to light with wavelength longer than $\lambda_c$. Either of these optional measures provide greater robustness of the device to the effect of any ambient light which has wavelength longer than $\lambda_c$.

The light 17 propagates through the first window 13, then through the gas or gas mixture 21 occupying the chamber, then through the second window 14 and finally towards the first photodetector 15. An optional second lens 22 may be positioned between the second window 14 and the first photodetector 15 to focus the light 17 towards the first photodetector 15.

The distance that the light 17 propagates through the gas or gas mixture 21 occupying the chamber 1 is L. L may be any value but is preferably between 1 cm and 200 cm. In this example L≈20 cm.

The first photodetector 15 is used to determine $I_1$ for the gas or gas mixture 21 which occupies the chamber 1. The power of the light 17 which is incident on the first window 13 ($I_0$), may be determined from the known characteristics of the light source 2 (for example, a known relationship between the electrical current supplied to the light source 2 and $I_0$). Alternatively, $I_0$ may be determined from an optional integrated photodetector 23 located in the proximity of the light source 2. Alternatively, if the optional second photodetector 20 is included then the power of light incident on said photodetector may be used to determine a value proportional to $I_0$. Consequently, the ratio $$\frac{I_1}{I_0},$$

or a value proportional to this ratio may be determined.

The apparatus 10 may be used to perform a method of measuring a concentration of a component of a gas mixture. In exemplary embodiments, the method may include the steps of: introducing a reference gas into a chamber; emitting light from a light source into the chamber to propagate through the reference gas, wherein light emitted from the light source includes a wavelength between 230 nm and 320 nm; detecting a portion of the light from the light source that has propagated through the reference gas in the chamber with a light sensor, and determining a first ratio of power of the light emitted from the light source to power of the light detected by the light sensor; introducing a measurement gas mixture into the chamber; emitting light from the light source into the chamber to propagate through the measurement gas mixture; detecting a portion of the light from the light source that has propagated through the measurement gas mixture in the chamber with the light sensor, and determining a second ratio of power of the light emitted from the light source to power of the light detected by the light sensor; and calculating a concentration of a component of the measurement gas mixture based on the first and second ratios.

For example, the apparatus 10 may be used to measure the concentration of acetone in exhaled breath in the following exemplary procedure, which is depicted in the flow chart of FIG. 8:

1. A reference gas enters the chamber 1 via the inlet valve 11. The reference gas may be ambient air.
2. The light source 2 is switched on, either in pulsed or continuous mode, to emit light 17. The ratio $$\left(\frac{I_1}{I_0}\right)_{Ref},$$

or a value proportional to this ratio may be determined using the first photodetector and optionally also the second photodetector.

3. Exhaled breath enters the chamber 1 via the inlet valve 11 and the reference gas exits the chamber via the outlet valve 12. A person may exhale directly into the apparatus, such that the exhaled breath enters the chamber 1, or the person may exhale into a separate container and the gas mixture from said container may then be transferred into the chamber 1.
4. The light source 2 is switched on, either in pulsed or continuous mode, to emit light 17. The ratio $$\left(\frac{I_1}{I_0}\right)_{Breath},$$

or a value proportional to this ratio may be determined using the first photodetector and optionally also the second photodetector.

5. An algorithm, such as the example in equation 8, may now be used to determine the concentration of acetone in the exhaled breath from the measurements of $$\left(\frac{I_1}{I_0}\right)_{Ref} \text{ and } \left(\frac{I_1}{I_0}\right)_{Breath}.$$

The algorithm may take as optional inputs any of the following for the reference gas and/or the exhaled breath: temperature; pressure; carbon dioxide sensor output; oxygen sensor output. Furthermore, the algorithm may take any of the following as optional inputs: the wavelength of the light source 2; users' characteristics; environment characteristics.

Figure 8:
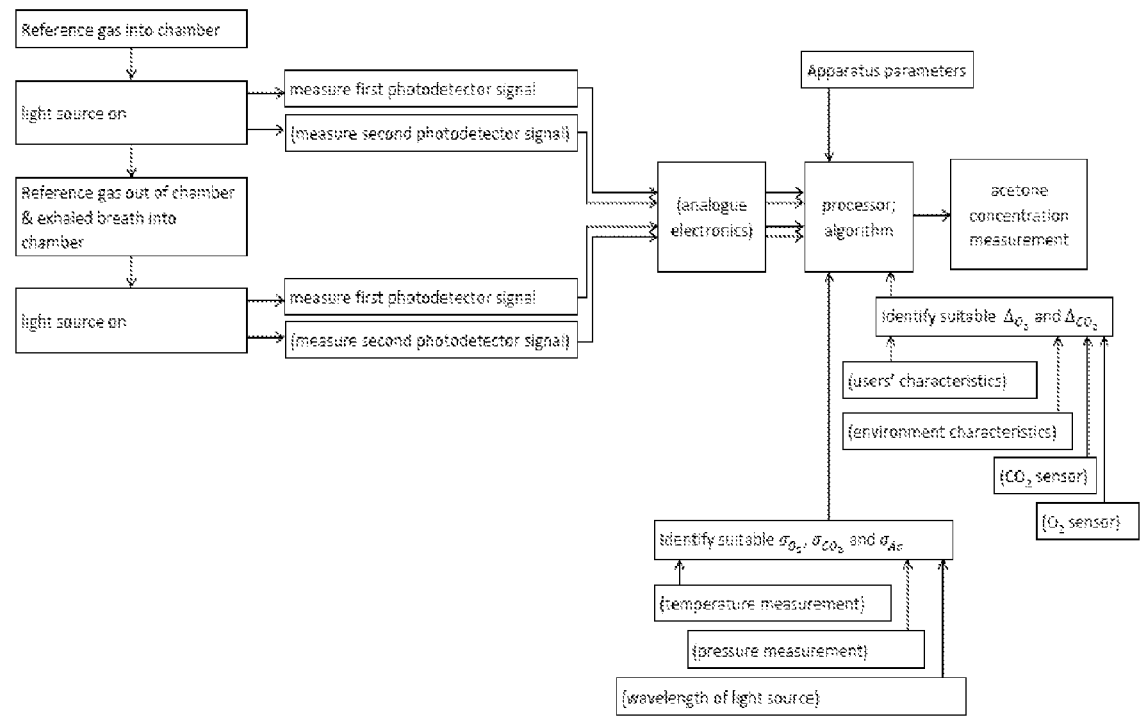
FIG. 8: A flow chart illustrating a method to determine the concentration of acetone in exhaled breath using an apparatus according to the invention.

As referenced above, this exemplary method is shown in FIG. 8 (optional steps are shown in parentheses). In the present example, an algorithm based on equation 8 is used with the following parameters:

$$\varepsilon = \varepsilon'; \Delta_{O_2} = \frac{21\% - 16\%}{100\%} \frac{N_A}{V_m}; \Delta_{CO_2} = \frac{0.04\% - 5\%}{100\%} \frac{N_A}{V_m},$$

$$L = 20 \text{ cm}; \sigma_{O_2} = 1.9 \times 10^{-25} \text{ cm}^2; \sigma_{CO_2} = 1.8 \times 10^{-25} \text{ cm}^2; \text{ and}$$

$$\sigma_{Ac} = 4.4 \times 10^{-20} \text{ cm}^2.$$

The algorithm may be implemented using a microprocessor 24 which uses the inputs of $$\left(\frac{I_1}{I_0}\right)_{Ref} \text{ and } \left(\frac{I_1}{I_0}\right)_{Breath}$$

and thereby provides a measurement of the concentration of acetone in the exhaled breath. The microprocessor 24 may further control other components in the apparatus, for example switching on the light source 2 as appropriate.

The measurement result can be displayed to the user via display (for example, a LCD display), or transmitted wirelessly to a portable device such as a cell phone, tablet computer or personal computer.

The measurement result may further add a recommendation concerning the significance of the measurement result for the person whose exhaled breath was analysed. For example, depending on the acetone concentration in the exhaled breath, the measurement result may be accompanied by a diagnosis indication or advice. In diabetes applications, an indication or advice such as: "no ketoacidosis", "mild ketoacidosis", "severe ketoacidosis" may be used. In weight management applications, an indication or advice such as: "low fat burning rate", "medium fat burning rate", and "high fat burning rate" may be used. The microprocessor 24 can be an integrated part of the breath analyser or a detachable unit, such as a laptop computer having an appropriate software and electronic interface.

The apparatus 10 provides a method to measure the concentration of acetone in exhaled breath with significant advantages over apparatuses described in the prior art.

Further optional improvements to the apparatus are also shown in FIG. 7. These include a temperature sensor 25 and pressure sensor 26 located, for example, inside chamber 1 to provide pressure and temperature measurements. The output from the temperature and/or pressure sensors may further be used in the algorithm to improve the accuracy of the acetone measurement result, for example by adjusting the assumed absorption cross section values ($\sigma_{O_2}$, $\sigma_{CO_2}$, $\sigma_{Ac}$) according to the temperature and pressure of the gas in the chamber, using a pre-determined database. Furthermore, pressure sensor 26 can also be used to regulate the air and breath pressure inside chamber 1 through controlling the inlet 11 and outlet 12 valves.

Figure 18:
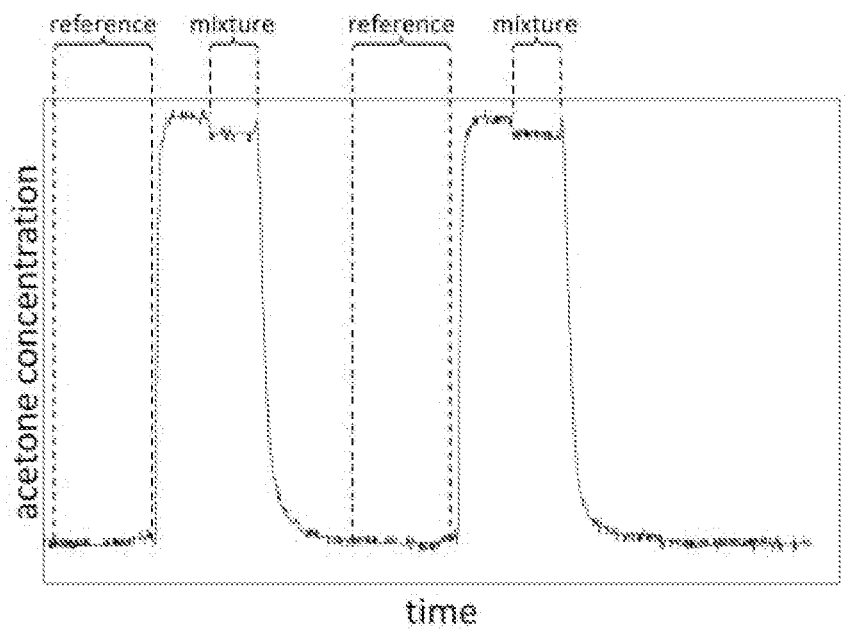
FIG. 18: An example of output of apparatus according to an embodiment of the invention

An example of the output of apparatus as described in the first example is shown in FIG. 18. In this example the apparatus included a LED emitting light with a central wavelength of approximately 283 nm and a spectral FWHM of approximately 12 nm. The plot in FIG. 18 shows the state of the sensor over a period of time: initially a reference gas (nitrogen) was introduced into the chamber (labelled "reference" in FIG. 18); then a gas mixture including acetone in nitrogen was introduced into the chamber (labelled "mixture"); then this process was repeated to test the reproducibility of the apparatus. Through use of the reference measurement the acetone concentration in the gas mixture was obtained with high accuracy for both gas mixtures, thereby proving the efficacy of sensing acetone concentration in a gas mixture using apparatus according to the first example of the invention.

EXAMPLE 2

Dual-Wavelength Sensor

Figure 9:
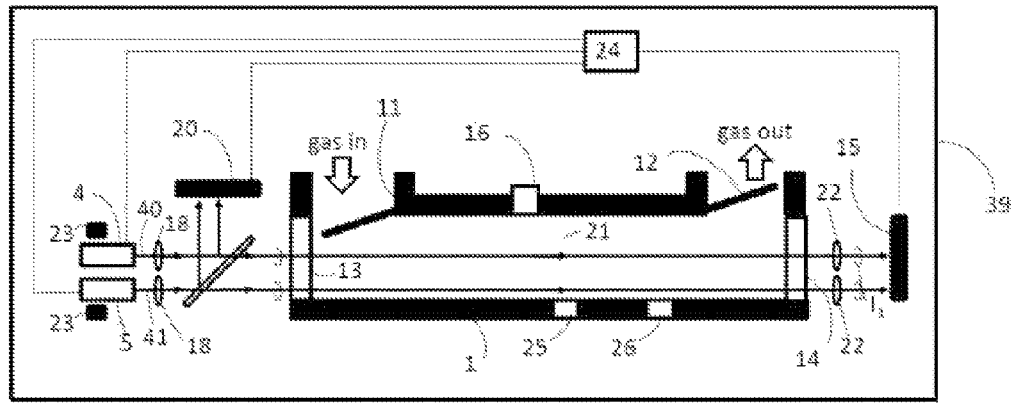
FIG. 9. An illustration of an apparatus used to measure acetone concentration in a gas mixture using a first light source and a second light source in an example of the invention

A second example of an apparatus to measure the concentration of acetone in exhaled breath is illustrated in FIG. 9. The second example has many features in common with the first example. These common features are labelled using the same numerical labels as for the first example and they will not be described in detail again. The apparatus 39 includes a chamber 1, an inlet valve 11, an outlet valve 12, a first window 13, a second window 14, a first light source 4, a second light source 5 and a first photodetector 15.

The first light source 4 emits light with wavelength or wavelengths between 230 nm and 320 nm. The second light source 5 emits light with wavelength or wavelengths between 230 nm and 320 nm which are different from the wavelength or wavelengths of light emitted by the first light source.

The first and second light sources may emit light with a single wavelength or light with a range of wavelengths about a central wavelength. The first and second light sources may emit light with linewidths between 5 nm and 30 nm. The first and second light sources may include one or more LEDs. For this example the first and second light sources each include one LED which contains $Al_yGa_{1-y}N$ material (where $0 \leq y \leq 1$). For this example the first light source contains an LED which emits light with a central wavelength ($\lambda_1$) of approximately 255 nm and the second light source contains an LED which emits light with a central wavelength ($\lambda_2$) of approximately 290 nm.

The first light source emits a first light 40 and the second light source emits a second light 41. The first light 40 propagates through the first window 13, then through the gas or gas mixture 21 occupying the chamber 1, then through the second window 14 and finally towards the first photodetector 15. The second light 41 also propagates through the first window 13, then through the gas or gas mixture 21 occupying the chamber 1, then through the second window 14 and finally towards the first photodetector 15. Optional second lenses 22 may be positioned between the second window 14 and the first photodetector 15 to focus the first light 40 and second light 41, respectively, towards the first photodetector 15.

The first light source 4 may be used to determine $$\left(\frac{I_1}{I_0}\right)^{\lambda_1}_{Ref} \text{ and } \left(\frac{I_1}{I_0}\right)^{\lambda_1}_{Breath}$$

using a procedure similar to the one described in the first example using the light source 2 (referring to equations 10-14). The second light source 5 may be used to determine $$\left(\frac{I_1}{I_0}\right)^{\lambda_2}_{Ref} \text{ and } \left(\frac{I_1}{I_0}\right)^{\lambda_2}_{Breath}$$

using a procedure similar to the one described in the first example using the light source 2.

In a preferred example, the first light source 4 and the second light source 5 are operated at different times to obtain the two separate measurements using a single photodiode in the photodetector. An alternative example uses separate photodiodes to measure the light from the first light source 4 and the second light source 5. In this case the first and second light sources may operate at the same time.

The apparatus 39 may be used to perform another method of measuring a concentration of a component of a gas mixture. In exemplary embodiments, the method may include the steps of: introducing a reference gas into a chamber; emitting light from a first light source and a second into the chamber to propagate through the reference gas, wherein light emitted from the first and second light sources each includes a wavelength between 230 nm and 320 nm; detecting a portion of the light from the first and second light sources that has propagated through the reference gas in the chamber with at least one light sensor, determining a first ratio of power of the light emitted from the first light source to power of the light from the first light source detected by the light sensor, and determining a second ratio of power of the light emitted from the second light source to power of the light from the second light source detected by the light sensor; introducing a measurement gas mixture into the chamber; emitting light from the first and second light sources into the chamber to propagate through the measurement gas mixture; detecting a portion of the light from the first and second light sources that has propagated through the measurement gas mixture in the chamber with the at least one light sensor; determining a third ratio of power of the light emitted from the first light source to power of the light from the first light source detected by the light sensor, and determining a fourth ratio of power of the light emitted from the second light source to power of the light from the second light source detected by the light sensor; and calculating a concentration of a component of the gas mixture based on the first, second, third, and fourth ratios.

For example, the apparatus 39 may be used to measure the concentration of acetone in exhaled breath in the following exemplary procedure, which is depicted in the flow chart of FIG. 10:

1. A reference gas enters the chamber 1 via the inlet valve 11. The reference gas may be ambient air.
2. The first light source 4 is switched on, either in pulsed or continuous mode, to emit first light 40. The ratio $$\left(\frac{I_1}{I_0}\right)^{\lambda_1}_{Ref},$$

or a value proportional to this ratio may be determined using the first photodetector and optionally also the second photodetector.
3. The second light source 5 is switched on, either in pulsed or continuous mode, to emit second light 41. The ratio $$\left(\frac{I_1}{I_0}\right)^{\lambda_2}_{Ref},$$

or a value proportional to this ratio may be determined using the first photodetector and optionally also the second photodetector.
4. Exhaled breath enters the chamber 1 via the inlet valve 11 and the reference gas exits the chamber via the outlet valve 12. A person may exhale directly into the apparatus, such that the exhaled breath enters the chamber 1, or the person may exhale into a separate container and the gas mixture from said container may then be transferred into the chamber 1.
5. The first light source 4 is switched on, either in pulsed or continuous mode, to emit first light 40. The ratio $$\left(\frac{I_1}{I_0}\right)^{\lambda_1}_{Breath},$$

or a value proportional to this ratio may be determined using the first photodetector and optionally also the second photodetector.

6. The second light source 5 is switched on, either in pulsed or continuous mode, to emit second light 41. The ratio $$\left(\frac{I_1}{I_0}\right)^{\lambda_2}_{Breath},$$

or a value proportional to this ratio may be determined using the first photodetector and optionally also the second photodetector.

7. An algorithm, such as the example in equations 10-14, may now be used to determine the concentration of acetone in the exhaled breath from the measurements of $$\left(\frac{I_1}{I_0}\right)^{\lambda_1}_{Ref}, \left(\frac{I_1}{I_0}\right)^{\lambda_2}_{Ref}, \left(\frac{I_1}{I_0}\right)^{\lambda_1}_{Breath} \text{ and } \left(\frac{I_1}{I_0}\right)^{\lambda_2}_{Breath}.$$

The algorithm may take as optional inputs any of the following for the reference gas and/or the exhaled breath: temperature; pressure; carbon dioxide sensor output; oxygen sensor output. Further, the algorithm may take any of the following as optional inputs: the wavelengths of the first light source 4 and the second light source 5; users' characteristics; environment characteristics.

Figure 10:
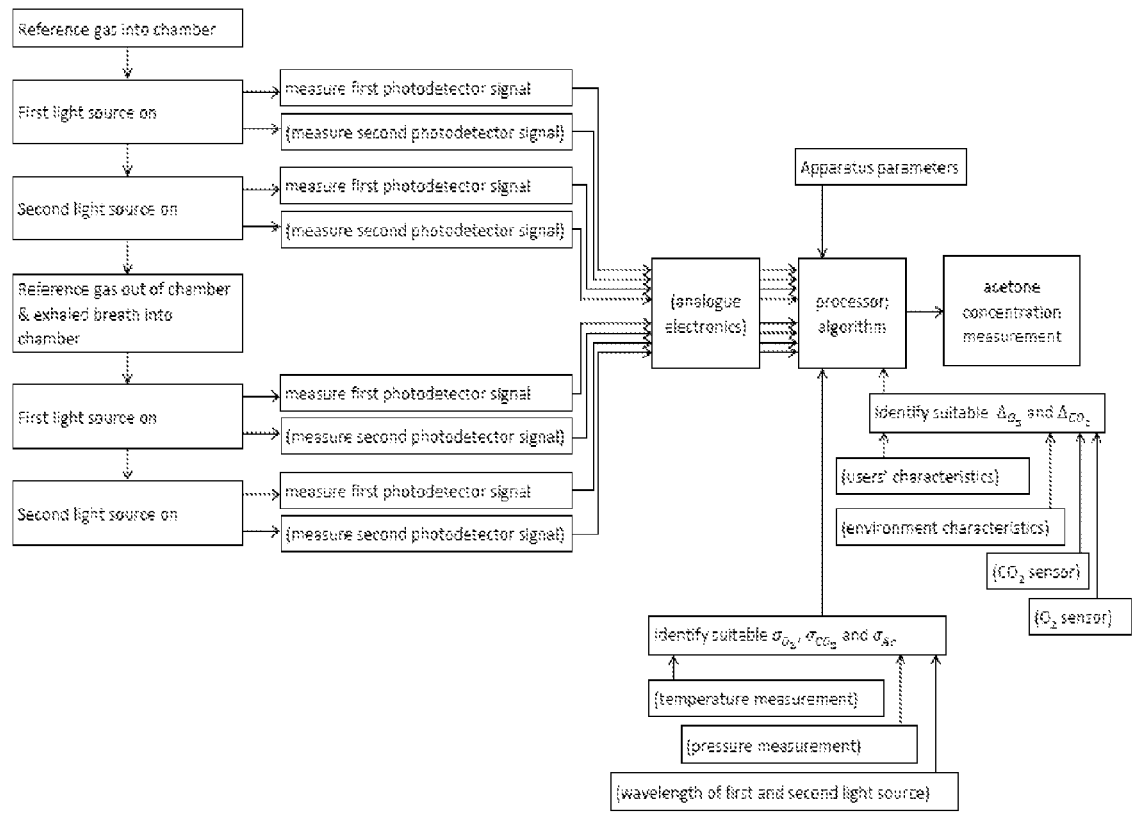
FIG. 10: A flow chart illustrating a method to determine the concentration of acetone in exhaled breath using an apparatus according to the invention.

As reference above, this exemplary procedure is shown in FIG. 10 (optional steps are shown in parentheses). In the present example, an algorithm based on equations 10-14 is used with the following parameters:

$$\Delta_{O_2} = \frac{21\% - 16\%}{100\%} \frac{N_A}{V_m}; \Delta_{CO_2} = \frac{0.04\% - 5\%}{100\%} \frac{N_A}{V_m}, L = 20 \text{ cm};$$

$$\sigma_{O_2} = 1.9 \times 10^{-25} \text{ cm}^2; \sigma_{CO_2} = 1.8 \times 10^{-25} \text{ cm}^2; \text{ and}$$

$$\sigma_{Ac} = 4.4 \times 10^{-20} \text{ cm}^2.$$

An advantage of the apparatus in example 2 over the apparatus described in example 1 is that the measured acetone concentration is more accurate when ozone is present.

EXAMPLE 3

Windows are Replaceable

In a third example, at least one of the first window 13 and the second window 14 may be removed from the apparatus and replaced during routine use of the apparatus. Replacement of the windows can be advantageous if any contamination has formed on the windows which causes significant absorption of UV light. In one implementation a disposable module which includes the first window 13 and the second window 14 may be removed from the apparatus and replaced.

EXAMPLE 4

LED and Photodetector Inside (No Windows)

Figure 11:
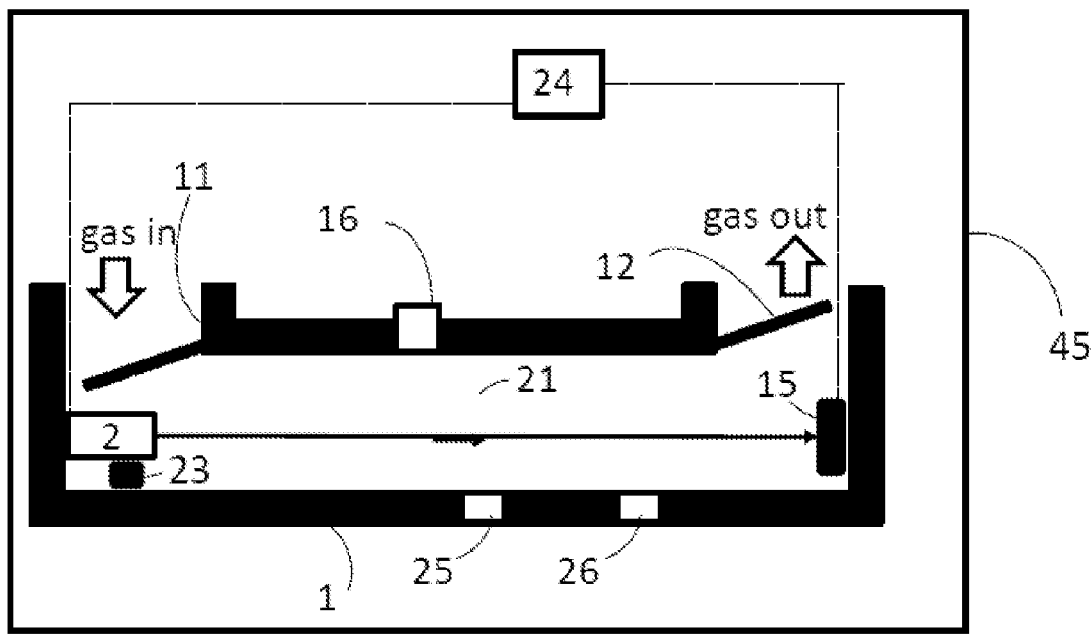
FIG. 11: An illustration of an apparatus used to measure acetone concentration in a gas mixture using a light source in an example of the invention

A fourth example of an apparatus to measure the concentration of acetone in exhaled breath is illustrated in FIG. 11. The fourth example has many features in common with the first example. These common features are labelled using the same numerical labels as for the first example and they will not be described in detail again.

A distinguishing feature of the fourth example is that the light source 2 and the first photodetector 15 are located inside the chamber 1. If the light source 2 is located inside the chamber 1 then the first window 13 that was used in the first example is no longer required. If the photodetector 15 is located inside the chamber 1 then the second window 14 that was used in the first example is no longer required. An advantage of the fourth example is that fewer components are required in the apparatus and therefore the cost is reduced.

EXAMPLE 5

Sensor Using Fluorescence

Figure 12:
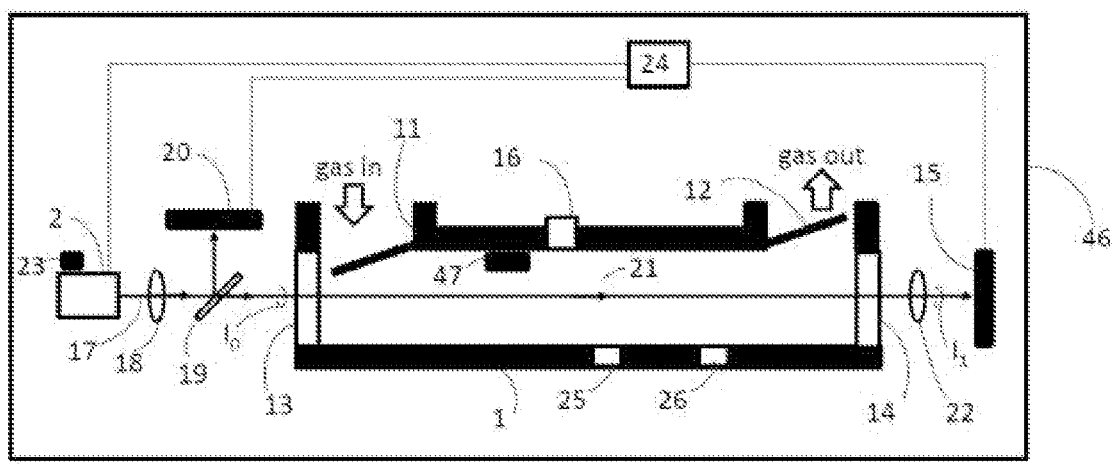
FIG. 12: An illustration of an apparatus used to measure acetone concentration in a gas mixture using a light source in an example of the invention

A fifth example of an apparatus to measure the concentration of acetone in exhaled breath is illustrated in FIG. 12. The fifth example has many features in common with the first example. These common features are labelled using the same numerical labels as for the first example and they will not be described in detail again.

A distinguishing feature of the fifth example is that a third photodetector 47 is included in the apparatus. The third photodetector 47 is sensitive to light with wavelength in the range 300 nm-400 nm and has very small or zero sensitivity to the light emitted by the light source 2. The third photodetector may include one or more optical filters which completely or substantially attenuates light emitted by the light source 2. A purpose of the third photodetector is to measure the intensity of light due to fluorescence from a component of the gas mixture that absorbs light emitted from the light source, such as fluorescence from acetone or other molecules in the gas mixture. The fluorescence from acetone or other molecules in the gas mixture is excited by the light emitted by the light source 2. The third photodetector 47 may include one or more optical filters which precisely select the fluorescence range to be measured. The light fluorescence intensity is directly proportional to the concentration of acetone or another molecule in the gas mixture and can be used to further improve the measurement accuracy. Fluorescence detection such as described in this example may further be combined with a design which includes at least two different light sources emitting different central wavelengths. In this case the at least two different central wavelengths may excite fluorescence from different molecules in the gas and this method may be used to further improve the accuracy of the sensor to determine the concentration of acetone.

EXAMPLE 6

Sensor with Multipass Cell

Figure 13:
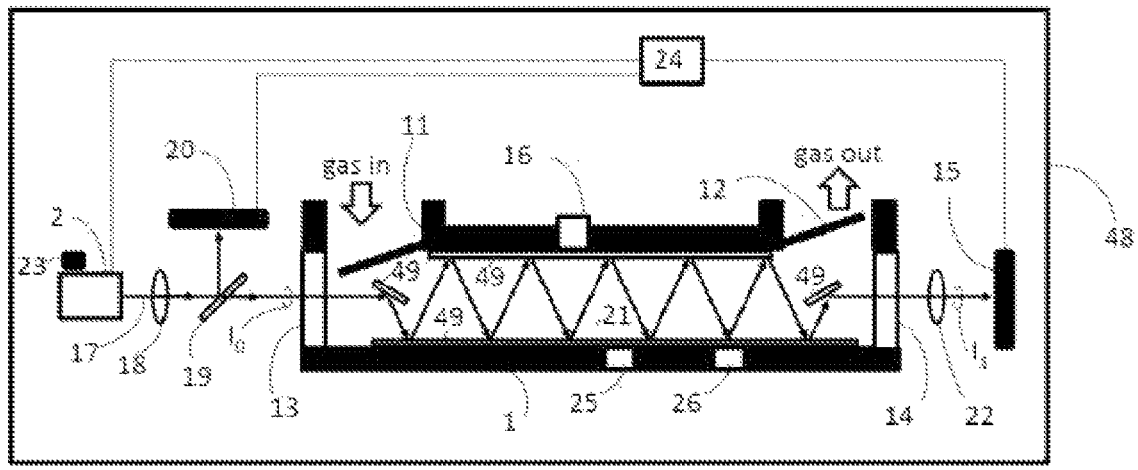
FIG. 13: An illustration of an apparatus used to measure acetone concentration in a gas mixture using a light source in an example of the invention

A sixth example of an apparatus to measure the concentration of acetone in exhaled breath is illustrated in FIG. 13. The sixth example has many features in common with the first example. These common features are labelled using the same numerical labels as for the first example and they will not be described in detail again.

A distinguishing feature of the sixth example is that the sensitivity of the apparatus to acetone is improved by increasing the absorption path length L using one or more mirror structures 49 to deflect the direction of the light within the chamber 1. There are many methods which can be used to increase the absorption path length L. One example is illustrated schematically in FIG. 13 in which high reflectivity mirrors 49 are placed inside the chamber 1 to fold the path of the light so that the path length for the light is significantly larger than the distance between the light source 2 and the first photodetector 15. The mirrors 49 may have a reflectivity to light emitted by the light source 2 which is at least 80%; preferably the reflectivity is at least 90% and most preferably the reflectivity is at least 99%. The sensitivity of the apparatus to measure small concentrations of acetone is increased when the path length for the light is longer. Therefore, an advantage of this sixth example is that the sensitivity of the apparatus to measure the concentration of acetone is increased but the overall size of the apparatus is not significantly increased.

EXAMPLE 7

Sensor with Resonant Cavity

Figure 14:
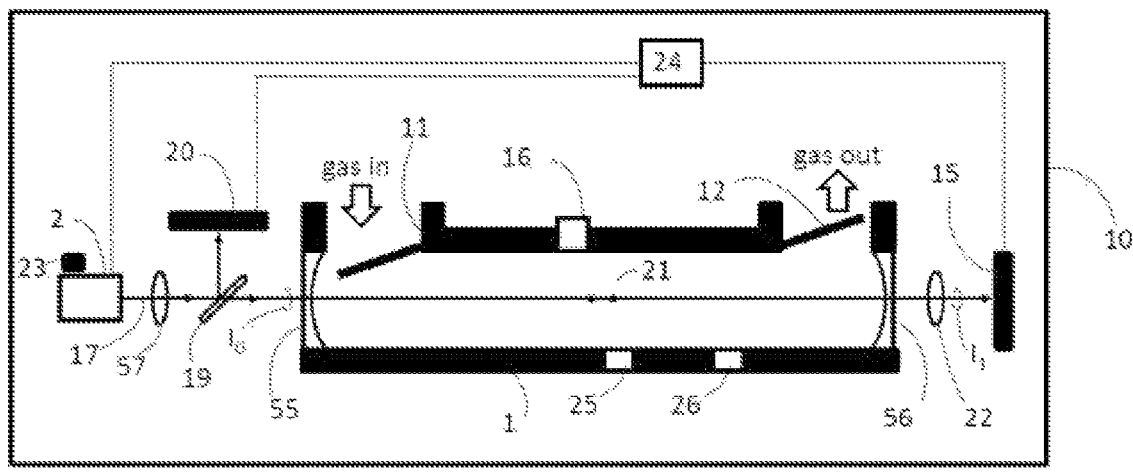
FIG. 14: An illustration of an apparatus used to measure acetone concentration in a gas mixture using a light source in an example of the invention

A seventh example of an apparatus to measure the concentration of acetone in exhaled breath is illustrated in FIG. 14. The seventh example has many features in common with the first example. These common features are labelled using the same numerical labels as for the first example and they will not be described in detail again.

A distinguishing feature of the seventh example, compared with the first example, is that the first window 13 is replaced by a first cavity mirror 55 and that the second window 14 is replaced by a second cavity mirror 56. The first and second cavity mirrors form an optical cavity for the light emitted by the light source 2. This type of arrangement is known as Cavity-Enhanced Absorption (CEA).

The shape of the first and second cavity mirrors are selected to provide a stable optical cavity for the light emitted by the first light source. The first and second cavity mirrors may be planar or may have a curved shape such as a concave shape. The first and second cavity mirrors may have different shapes.

In this example the first and second cavity mirrors are plano-concave shape. The mirrored surface is the concave side of each cavity mirror and this forms an inside wall for the chamber 1; the planar surface forms an exterior wall. The radius of curvature of the concave surface of each lens is approximately 50 cm, and the distance between the concave mirrors is approximately 25 cm. The reflectivity of the first and second cavity mirrors to light emitted by the light source 2 may be at least 90% and may be approximately 99% in a preferred example.

An optional lens 57 is positioned between the light source 2 and the first cavity mirror 55 to shape the beam of light emitted by the light source 2 so that the broadband resonance of the light within the cavity between the first and second cavity mirrors is strong.

The light emitted by the light source 2 is coupled into the cavity through the first cavity mirror 55 and may propagate between the first and second cavity mirrors many times, thereby providing a long effective path length for the light within the gas held in the chamber. A fraction of light which is circulating in the cavity is coupled out of the cavity through the second cavity mirror 56 and is detected at the first photodetector.

The light which is detected by the first photodetector may have an effective path length through the gas in the chamber which is many times higher than the distance between the first and second cavity mirrors. For example, and depending on the shape of the cavity mirrors, the reflectivity of the cavity mirrors and the action of the optional lens 57, the effective path length may be more than 10 times higher, more than 100 times higher or more than 1000 times higher.

EXAMPLE 8

Sensor with Heating Element (Remove Moisture)

Figure 19:
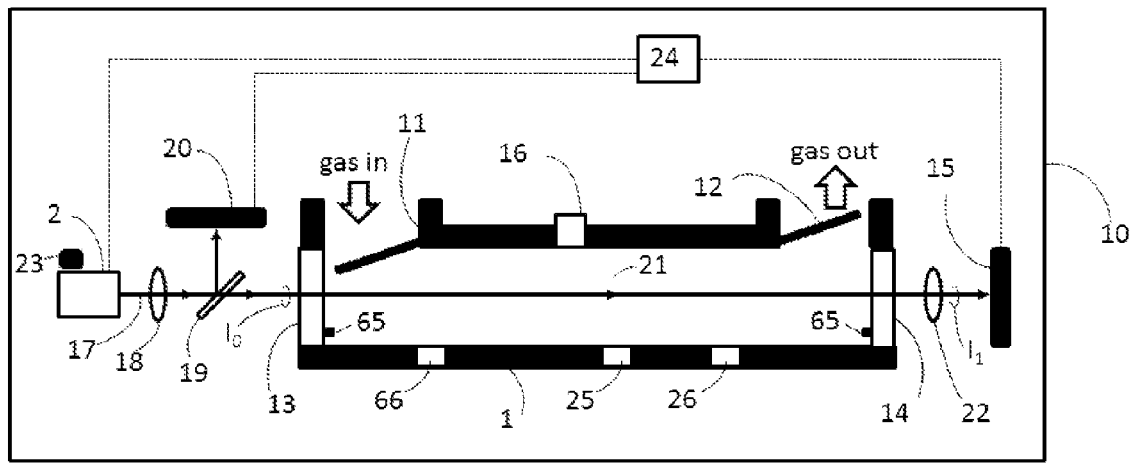
FIG. 19: An illustration of an apparatus used to measure acetone concentration in a gas mixture using a light source in an example of the invention

In an eighth example of the apparatus, a heating element, is included in order to heat up the gas sample (reference or breath) and/or to heat surfaces in contact with gas sample to a temperature higher than the ambient temperature or higher than the temperature of the reference gas or exhaled breath. An example is illustrated in FIG. 19. The apparatus is similar to the first example. A heating element 65 may be located near to a component of the apparatus, or attached to a surface of the apparatus, or embedded within a component of the apparatus. The heating element 65 may be used to heat the component of the apparatus. For example, the heating element 65 may be attached to the surface of one or both of the windows 13,14 (as shown in the example in FIG. 19), and used to heat the windows. The apparatus may also include a heating element 66 which is used to heat the gas within the chamber 1.

The heating element may be electrical (for example, an electrical resistance heater), or optical (for example, an infra red light source). In one example, one or more electrical resistance heaters may be attached to the surface of one or each of the first window and second window. In another example, one or more electrical resistance heaters may be embedded within one or each of the first window and second window.

An advantage of the eighth example is that the heating function can prevent condensation of moisture on surfaces in contact with the gas sample, such as the first and second windows.

EXAMPLE 9

Sensor with Light Tight Valves

Figure 15:
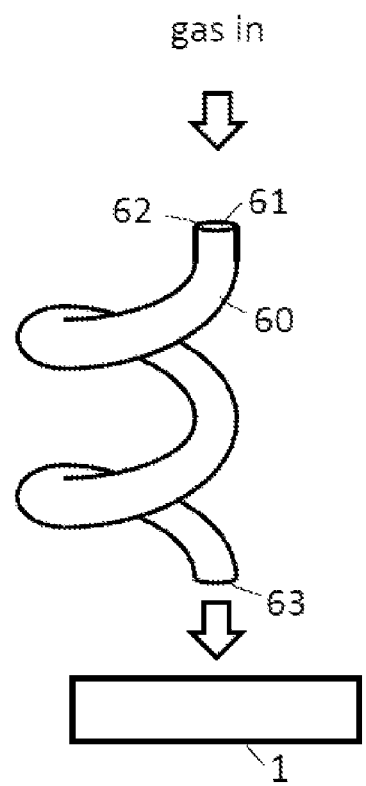
FIG. 15: An illustration of a valve

In a ninth example of the apparatus, at least one of the inlet valve 11 and the outlet valve 12 are light tight valves designed to prevent ambient light from propagating into the chamber 1 even when the valves are open to enable gas to flow through them. An exemplary light tight valve is illustrated in FIG. 15. A suitable valve includes a channel 60 with interior walls 61 which have a low reflectivity (for example, less than 10% and preferably less than 1%) to light with at least some light with wavelength between 300 nm and 700 nm. Gas flows through the channel from an entrance 62 to an exit 63 and then towards the chamber 1. Preferably the transmission of light with wavelengths between 300 nm and 700 nm between the entrance 62 and the exit 63 is less than 1%, and most preferably less than 0.01%.

In one example, the channel 60 changes direction through at least 360°, and preferably at least 720° between the start and end of the channel. FIG. 15 shows an example of a suitable design for a valve where the channel follows or has a "pigtail" spiral shape of this type.

Figure 16:
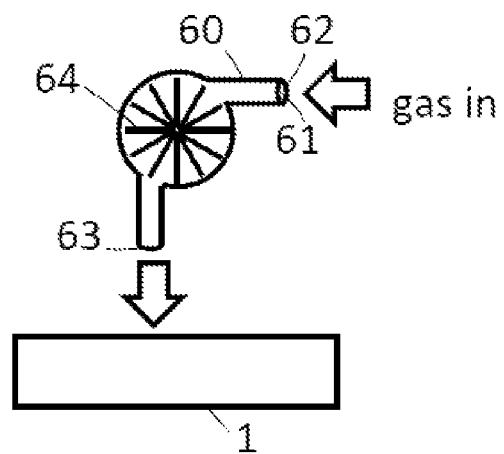
FIG. 16: An illustration of a valve with a moving component.

In another example, illustrated in FIG. 16, the channel 60 may include a moving component 64, which enables gas to flow between the entrance 62 and the exit 63 but reduces the transmission of at least some light with wavelength between 300 nm and 700 nm between the entrance 62 and the exit 63.

An advantage of the ninth embodiment is that the ambient light level in the chamber is also very low so that measurements of the absorption of UV light can be made as gas flows into the cell and it is not essential to close the inlet or outlet valves to obtain a measurement of the absorption of UV light.

EXAMPLE 10

Sensor with Particle Filter

Figure 20:
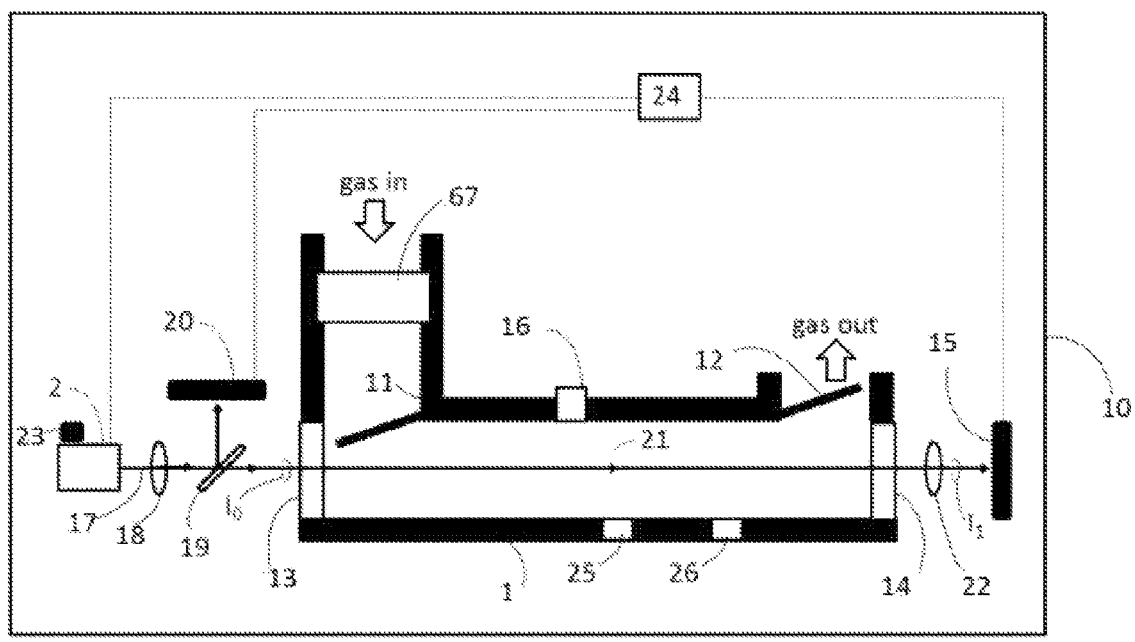
FIG. 20: An illustration of an apparatus used to measure acetone concentration in a gas mixture using a light source in an example of the invention

In a tenth example, a dust or particle filter 67 is included close to the inlet valve 11 in order to clean the gas from dust and particles which could contaminate the chamber and optics and may lead to interference with the measurements. The filter may also be used to remove moisture from the gas/breath. The filter may also be used to reduce the concentration of one or more gases. An illustration of this example is shown in FIG. 20, where the filter 67 acts on gas before the gas is introduced into the chamber 1 through the inlet valve 11.

Although the invention and examples 1-10 have been described with reference to breath components which absorb in the UV portion of the electromagnetic spectrum the invention is not limited to this, and the invention may be applied to other breath components of interest that absorb in other regions of the electromagnetic spectrum provided suitable LED sources exist in that region of the spectrum. Furthermore, the invention is not restricted to measurement of acetone only in exhaled breath: the invention may also be used to measure the concentration of acetone in other applications.

An aspect of the invention, therefore, is a measurement device for measuring a concentration of a component of a gas mixture. In exemplary embodiments, the measurement device includes a chamber for receiving the gas mixture, at least one light source that emits light into the chamber, the emitted light including a wavelength between 230 nm and 320 nm, at least one light sensor that detects a portion of the light from the light source that has propagated through the gas mixture in the chamber, and a processor configured to determine the concentration of the component of the gas mixture based on the portion of the light emitted from the light source that is detected by the light sensor.

In an exemplary embodiment of the measurement device, the at least one light source comprises a light emitting diode (LED) having a central wavelength of light emission between 270 nm and 320 nm, and a linewidth of light emission of less than 50 nm.

In an exemplary embodiment of the measurement device, the at least one light source comprises a first light source including a LED with a central wavelength of light emission between 240 nm and 270 nm, and a second light source including a LED with a central wavelength of light emission between 270 nm and 300 nm, and the LEDs of the first and second light sources each has a linewidth of light emission of less than 50 nm.

In an exemplary embodiment of the measurement device, the at least one light source includes an LED of an $Al_y In_x Ga_{1-x-y} N$ material where $0 \leq x \leq 1$ and $0 \leq y \leq 1$.

In an exemplary embodiment of the measurement device, the chamber has a first window for transmitting light from the light source into the chamber, and a second window for transmitting light from the chamber to the light sensor, wherein the first window and the second window comprise a disposable window module that is removable for replacement.

In an exemplary embodiment of the measurement device, the chamber has a first cavity mirror for transmitting light from the light source into the chamber, and a second cavity mirror for transmitting light from the chamber to the light sensor, wherein the first and second cavity mirrors form an optical cavity to increase a path length of the light emitted from the light source.

In an exemplary embodiment of the measurement device, the at least one light sensor further comprises a photodetector for detecting light due to fluorescence from the component of the gas mixture absorbing the light emitted from the light source.

In an exemplary embodiment of the measurement device, the chamber includes a mirror structure that reflects light within the chamber to increase a path length of the light emitted from the light source.

In an exemplary embodiment of the measurement device, the chamber includes a heating element for heating a surface of the chamber.

In an exemplary embodiment of the measurement device, the chamber includes an inlet valve for introducing gas into the chamber, and an outlet valve for venting gas from the chamber, wherein the inlet and outlet valves are light tight valves.

In an exemplary embodiment of the measurement device, the processor is configured to determine a total concentration of one or more ketones in the gas mixture.

In an exemplary embodiment of the measurement device, the gas mixture is exhaled breadth, and the processor is configured to determine a total concentration of the one or more ketones in the exhaled breath.

In an exemplary embodiment of the measurement device, the one or more ketones comprises acetone.

Another aspect of the invention is a first method of measuring a concentration of a component of a gas mixture. In exemplary embodiments, the first method includes the steps of: introducing a reference gas into a chamber; emitting light from a light source into the chamber to propagate through the reference gas, wherein light emitted from the light source includes a wavelength between 230 nm and 320 nm; detecting a portion of the light from the light source that has propagated through the reference gas in the chamber with a light sensor, and determining a first ratio of power of the light emitted from the light source to power of the light detected by the light sensor; introducing a measurement gas mixture into the chamber; emitting light from the light source into the chamber to propagate through the measurement gas mixture; detecting a portion of the light from the light source that has propagated through the measurement gas mixture in the chamber with the light sensor, and determining a second ratio of power of the light emitted from the light source to power of the light detected by the light sensor; and calculating a concentration of a component of the measurement gas mixture based on the first and second ratios.

Another aspect of the invention is a second method of measuring a concentration of a component of a gas mixture. In exemplary embodiments, the second method includes the steps of: introducing a reference gas into a chamber; emitting light from a first light source and a second light source into the chamber to propagate through the reference gas, wherein light emitted from the first and second light sources each includes a wavelength between 230 nm and 320 nm; detecting a portion of the light from the first and second light sources that has propagated through the reference gas in the chamber with at least one light sensor, determining a first ratio of power of the light emitted from the first light source to power of the light from the first light source detected by the light sensor, and determining a second ratio of power of the light emitted from the second light source to power of the light from the second light source detected by the light sensor; introducing a measurement gas mixture into the chamber; emitting light from the first and second light sources into the chamber to propagate through the measurement gas mixture; detecting a portion of the light from the first and second light sources that has propagated through the measurement gas mixture in the chamber with the at least one light sensor; determining a third ratio of power of the light emitted from the first light source to power of the light from the first light source detected by the light sensor, and determining a fourth ratio of power of the light emitted from the second light source to power of the light from the second light source detected by the light sensor; and calculating a concentration of a component of the gas mixture based on the first, second, third, and fourth ratios.

In exemplary embodiments of such methods, the reference gas is air.

In exemplary embodiments of such methods, the measurement gas mixture is exhaled breadth, and the component of the measurement gas mixture for which concentration is determined is a ketone.

In exemplary embodiments of such methods, the determination of the ketone concentration is further based on concentrations of one or more other gas components in the gas mixture or reference gas, and wherein the concentrations of the one or more other gas components are determined by at least one of sensor measurements, user characteristics, or environmental characteristics.

In exemplary embodiments of such methods, the methods further include the step of using the ketone concentration for at least one of diabetes diagnosis, diagnosis of ketoacidosis, fat burning measurement, or weight loss management.

In exemplary embodiments of such methods, the methods further include the step of outputting a recommendation for a user action.

Another aspect of the invention is a method of performing a breath analysis to determine acetone concentration for medical diagnostics. In exemplary embodiments, the method of breath analysis includes the steps of: introducing a reference gas into a chamber; emitting light from a light source into the chamber to propagate through the reference gas, wherein light emitted from the light source includes a wavelength between 230 nm and 320 nm; detecting a portion of the light from the light source that has propagated through the reference gas in the chamber with a light sensor, and determining a first ratio of power of the light emitted from the light source to power of the light detected by the light sensor; introducing exhaled breath into the chamber; emitting light from the light source into the chamber to propagate through the exhaled breath; detecting a portion of the light from the light source that has propagated through the exhaled breath in the chamber with the light sensor, and determining a second ratio of power of the light emitted from the light source to power of the light detected by the light sensor; and calculating a concentration of acetone in the exhaled breath based on the first and second ratios.

In an exemplary embodiment of the method of breath analysis, the determination of the acetone concentration is further based on concentrations of one or more other gas components in the gas mixture or reference gas, and wherein the concentrations of the one or more other gas components are determined by at least one of sensor measurements, user characteristics, or environmental characteristics.

In an exemplary embodiment of the method of breath analysis, the reference gas is air.

In an exemplary embodiment of the method of breath analysis, the method further includes the step of using the acetone concentration for at least one of diabetes diagnosis, diagnosis of ketoacidosis, fat burning measurement, or weight loss management.

In an exemplary embodiment of the method of breath analysis, the method further includes the step of outputting a recommendation for a user action.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

This invention can be used for the following applications:
Diabetes Diagnosis and Screening
Health/Diet Support, Weight Monitor
Prevention Ketoacidosis
Insulin Management
Blood Glucose monitoring and management

What is claimed is:

1. A measurement device for measuring a concentration of a component of a gas mixture comprising:
   a chamber for receiving the gas mixture;
   at least one light source that emits light into the chamber, the emitted light including a wavelength between 230 nm and 320 nm;
   at least one light sensor that detects a portion of the light from the light source that has propagated through the gas mixture in the chamber; and
   a processor configured to determine the concentration of the component of the gas mixture based on the portion of the light emitted from the light source that is detected by the light sensor;
   wherein the at least one light source comprises a first light source including a LED with a central wavelength of light emission between 240 nm and 270 nm, and a second light source including a LED with a central wavelength of light emission between 270 nm and 300 nm, and
   wherein the LEDs of the first and second light sources each has a linewidth of light emission of less than 50 nm.

2. The measurement device of claim 1, wherein the at least one light source includes an LED of an $Al_yIn_xGa_{1-x-y}N$ material where $0 \leq x \leq 1$ and $0 \leq y \leq 1$.

3. The measurement device of claim 1, wherein the chamber has a first window for transmitting light from the light source into the chamber, and a second window for transmitting light from the chamber to the light sensor, wherein the first window and the second window comprise a disposable window module that is removable for replacement.

4. The measurement device of claim 1, wherein the chamber has a first cavity mirror for transmitting light from the light source into the chamber, and a second cavity mirror for transmitting light from the chamber to the light sensor, wherein the first and second cavity mirrors form an optical cavity to increase a path length of the light emitted from the light source.

5. The measurement device of claim 1, wherein the at least one light sensor further comprises a photodetector for detecting light due to fluorescence from the component of the gas mixture absorbing the light emitted from the light source.

6. The measurement device of claim 1, wherein the chamber includes a mirror structure that reflects light within the chamber to increase a path length of the light emitted from the light source.

7. The measurement device of claim 1, wherein the chamber includes a heating element for heating a surface of the chamber.

8. The measurement device of claim 1, wherein the chamber includes an inlet valve for introducing gas into the chamber, and an outlet valve for venting gas from the chamber, wherein the inlet and outlet valves are light tight valves.

9. The measurement device of claim 1, wherein the processor is configured to determine a total concentration of one or more ketones in the gas mixture.

10. The measurement device of claim 9, wherein the gas mixture is exhaled breath, and the processor is configured to determine a total concentration of the one or more ketones in the exhaled breath.

11. The measurement device of claim 9, wherein the one or more ketones comprises acetone.

* * * * *